(12) United States Patent
Hee-Hanson et al.

(10) Patent No.: US 12,274,874 B1
(45) Date of Patent: Apr. 15, 2025

(54) INJECTOR DEVICE

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/594,643

(22) Filed: Mar. 4, 2024

(51) Int. Cl.
*A61M 5/32* (2006.01)

(52) U.S. Cl.
CPC ........ *A61M 5/3243* (2013.01); *A61M 5/3202* (2013.01); *A61M 5/3245* (2013.01); *A61M 2205/0216* (2013.01)

(58) Field of Classification Search
CPC ........ A61M 2205/0216; A61M 5/3202; A61M 5/3205; A61M 5/321; A61M 5/3243; A61M 5/3245; A61M 5/3275
See application file for complete search history.

(56) References Cited

U.S. PATENT DOCUMENTS

| | | | |
|---|---|---|---|
| 5,356,387 A | 10/1994 | Sirbola | |
| 7,597,685 B2 | 10/2009 | Olson | |
| 8,048,035 B2 * | 11/2011 | Mesa | A61M 5/3202 604/198 |
| 8,945,063 B2 | 2/2015 | Wotton et al. | |
| 9,216,256 B2 | 12/2015 | Olson et al. | |
| 9,687,607 B2 | 6/2017 | Brereton et al. | |
| 10,569,019 B2 * | 2/2020 | Hirschel | A61M 5/24 |
| 10,799,647 B2 | 10/2020 | Hostettler et al. | |

(Continued)

FOREIGN PATENT DOCUMENTS

| | | | |
|---|---|---|---|
| CH | 705345 A2 | 2/2013 | |
| CH | 705992 A2 | 6/2013 | |

(Continued)

OTHER PUBLICATIONS

Needle-based injection systems for medical use Requirements and test methods, Part 1: Needle injection systems, ISO 11608 1:2014(E), Third Edition, Switzerland, ISO, Dec. 15, 2014, pp. 1-13.

(Continued)

*Primary Examiner* — Shefali D Patel
(74) *Attorney, Agent, or Firm* — Fish & Richardson P.C.

(57) ABSTRACT

A medicament delivery device for reducing a force required to activate the device includes a needle disposed at a distal end of the device, a needle cover, and a body. The needle cover is axially movable relative to the body between an initial position in which the needle cover covers the needle and an activated position for dispensing a medicament. The needle protrudes from a distal end of the needle cover when the needle cover is in the activated position. The medicament delivery device includes a carrier configured to support a syringe. The carrier is disposed within the needle cover and includes a deformable element configured to change from a first configuration in which the deformable element is engaged with the needle cover to a second configuration in which the deformable element is not engaged with the needle cover.

21 Claims, 15 Drawing Sheets

(56) References Cited

U.S. PATENT DOCUMENTS

| | | |
|---|---|---|
| 11,116,911 B2 | 9/2021 | Wu |
| 11,383,044 B2 | 7/2022 | Tschirren et al. |
| 2004/0039336 A1 | 2/2004 | Amark et al. |
| 2005/0101919 A1 | 5/2005 | Brunnberg |
| 2007/0060840 A1 | 3/2007 | Conway |
| 2007/0112310 A1 | 5/2007 | Lavi et al. |
| 2007/0239117 A1 | 10/2007 | Chelak et al. |
| 2013/0289525 A1 | 10/2013 | Kemp et al. |
| 2017/0106146 A1 | 4/2017 | Folk et al. |
| 2019/0358400 A1 | 11/2019 | Nakamura et al. |
| 2020/0046909 A1 | 2/2020 | Hommann et al. |
| 2020/0289754 A1 | 9/2020 | Liscio et al. |
| 2021/0361881 A1 | 11/2021 | Garson et al. |
| 2021/0393886 A1 | 12/2021 | Nicolas et al. |

FOREIGN PATENT DOCUMENTS

| | | |
|---|---|---|
| EP | 3381490 B1 | 9/2020 |
| WO | WO 2002/047746 A1 | 6/2002 |
| WO | WO 2010/136077 A1 | 12/2010 |
| WO | WO 2018/011417 A1 | 1/2018 |
| WO | WO 2021/160540 A1 | 8/2021 |
| WO | WO 2021/197804 A1 | 10/2021 |
| WO | WO 2022/069617 A1 | 4/2022 |
| WO | WO 2022/184388 A1 | 9/2022 |
| WO | WO 2022/223789 A1 | 10/2022 |
| WO | WO 2023/057578 A1 | 4/2023 |

OTHER PUBLICATIONS

U.S. Appl. No. 18/594,556, filed Mar. 4, 2024, Alexander Hee-Hanson.

U.S. Appl. No. 18/594,683, filed Mar. 4, 2024, Alexander Hee-Hanson.

U.S. Appl. No. 18/594,597, filed Mar. 4, 2024, Alexander Hee-Hanson.

* cited by examiner

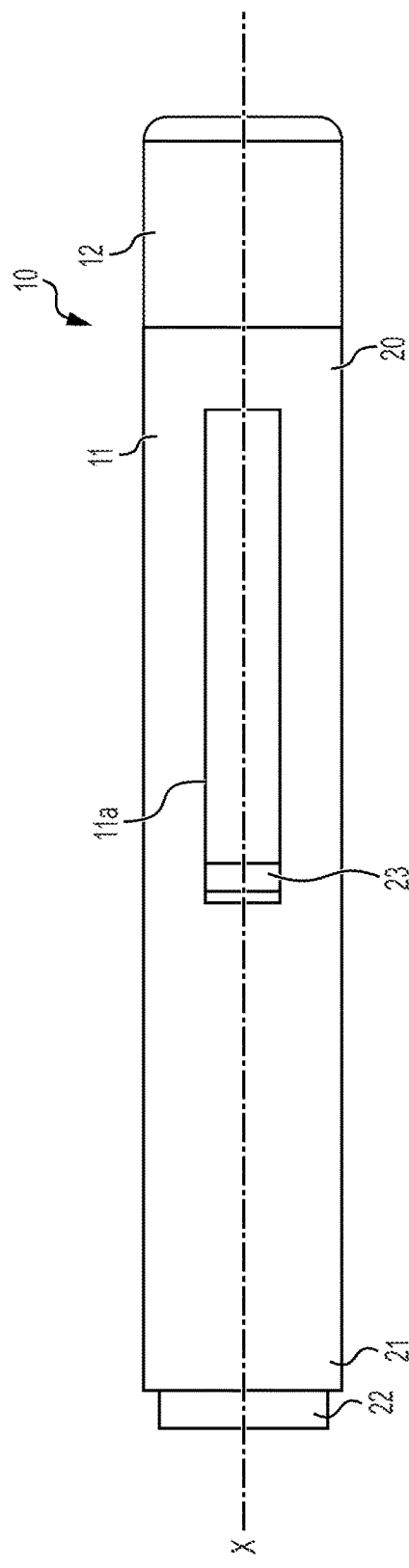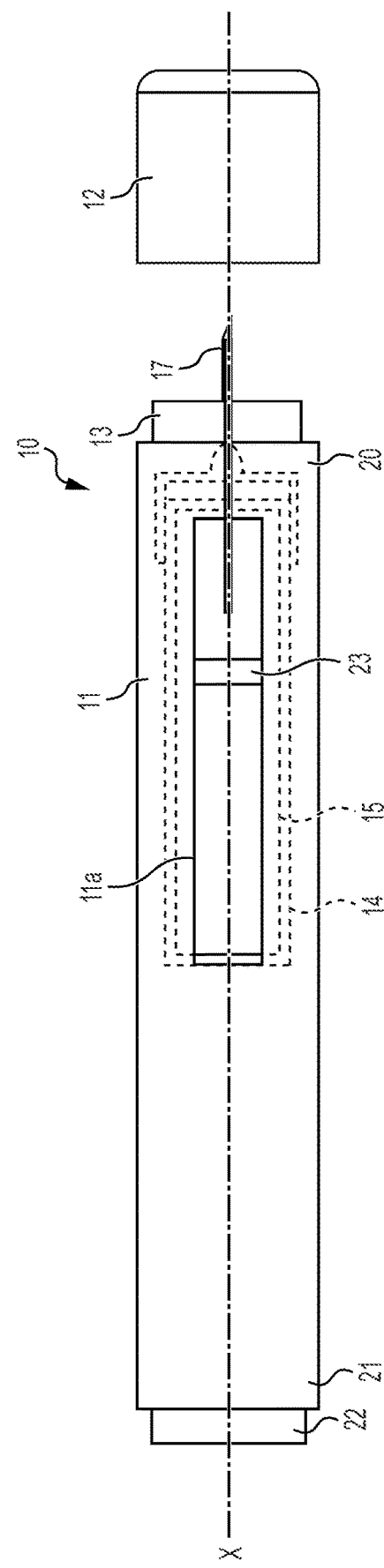

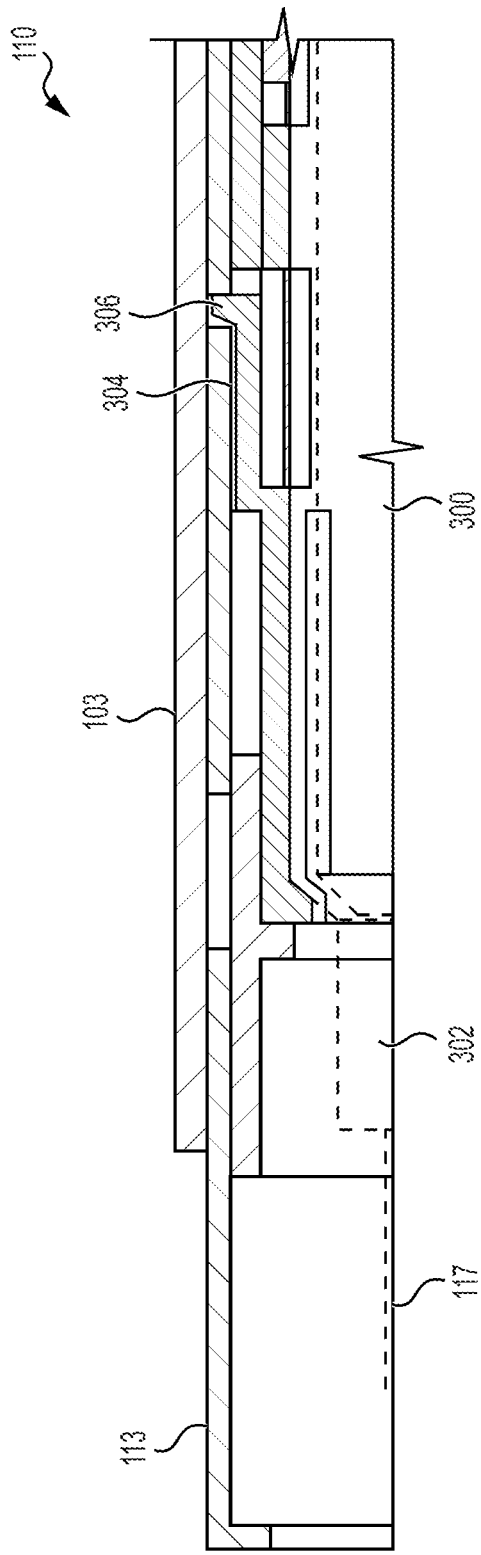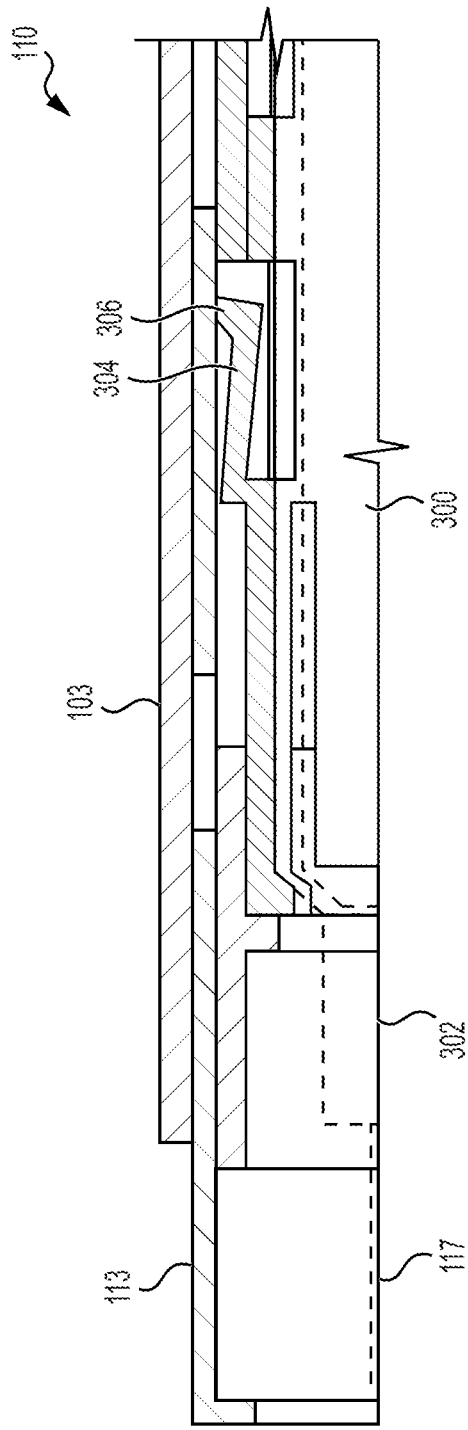

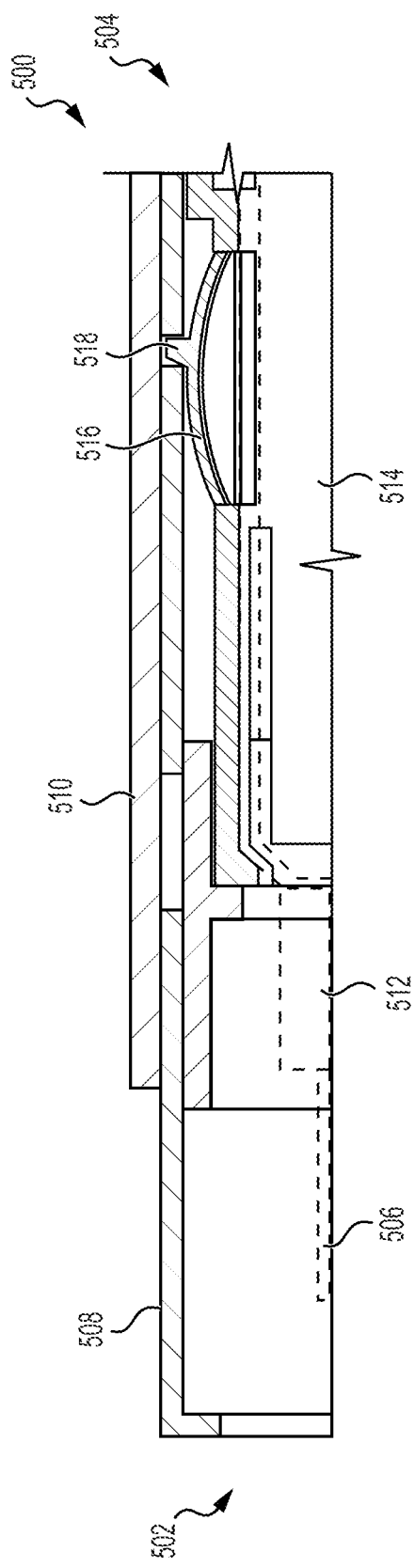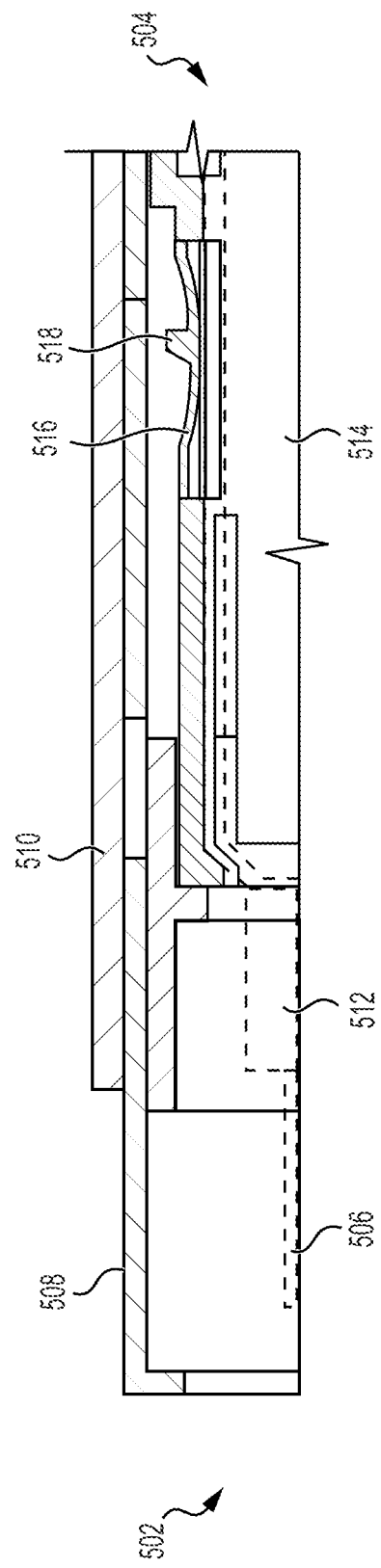
FIG. 5A
FIG. 5B

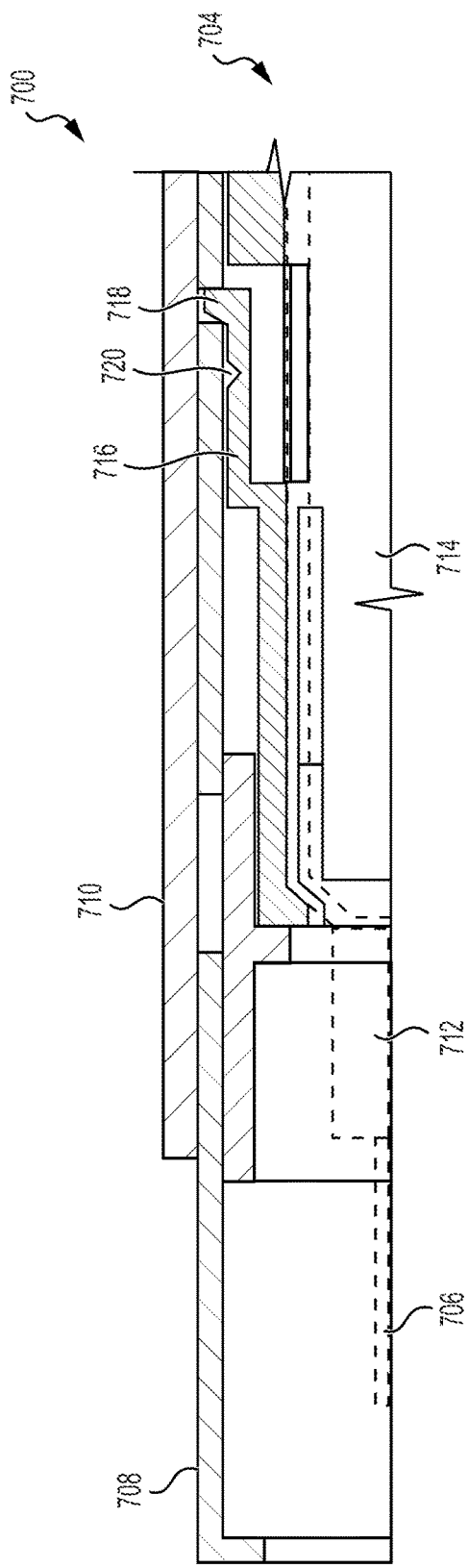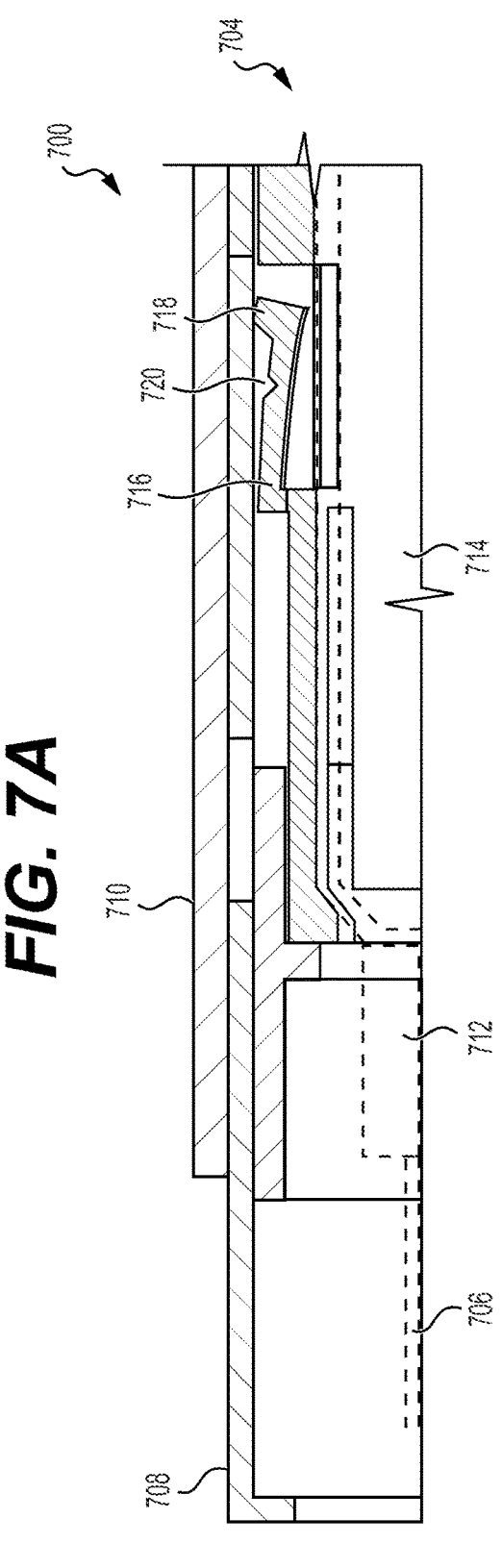

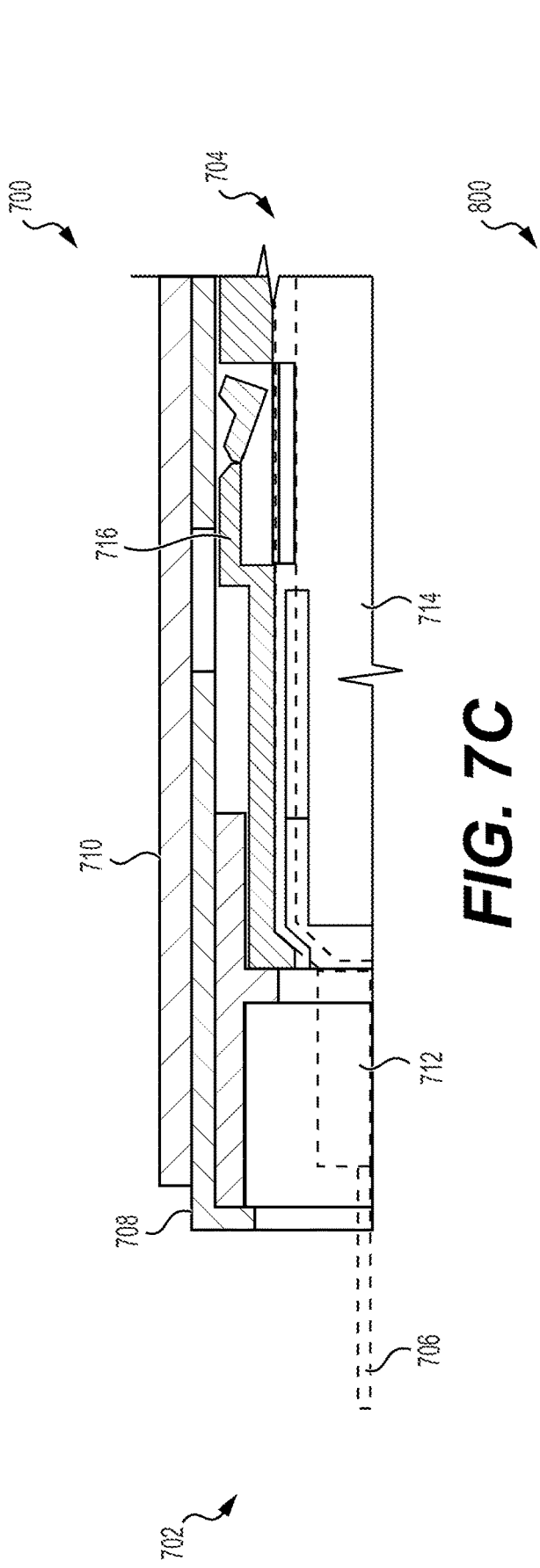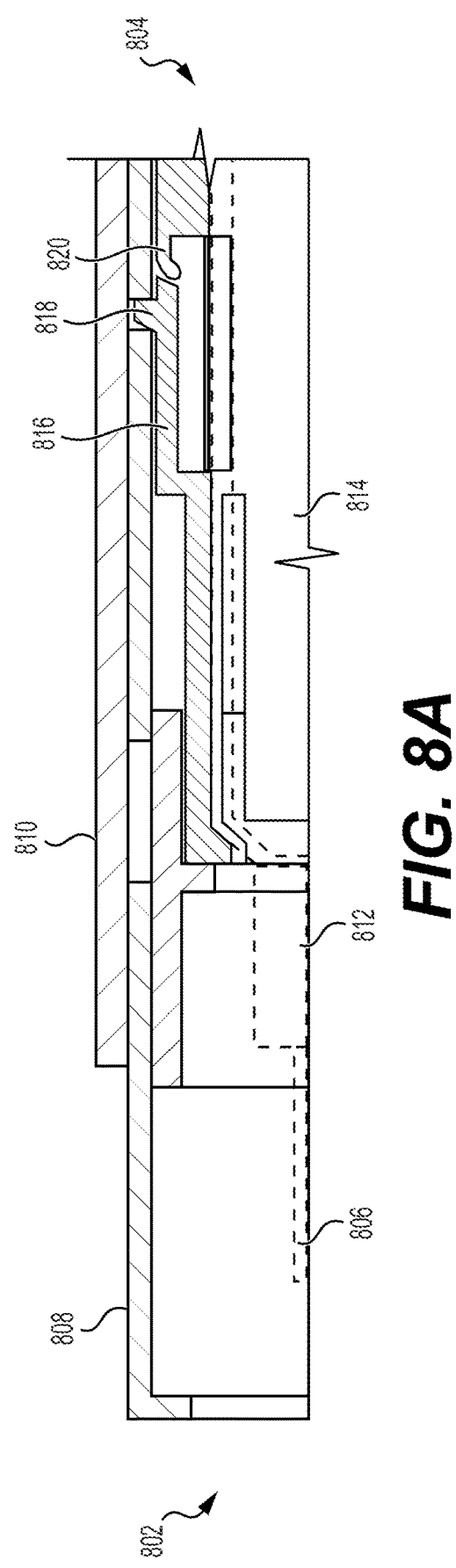

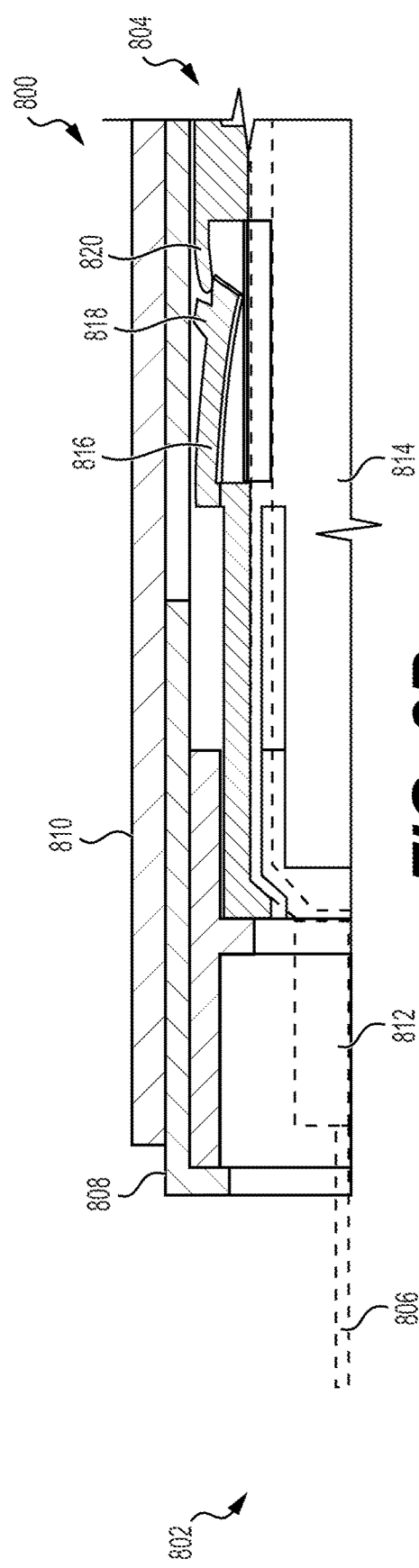
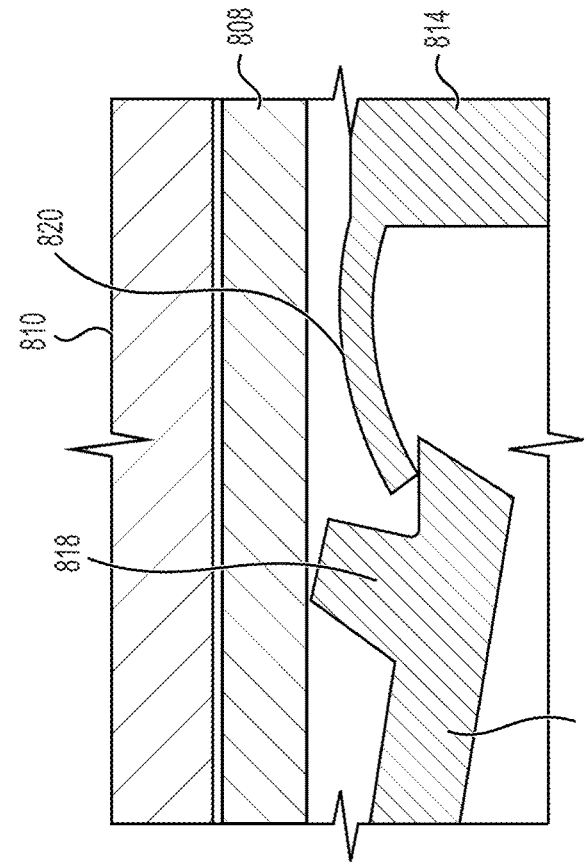
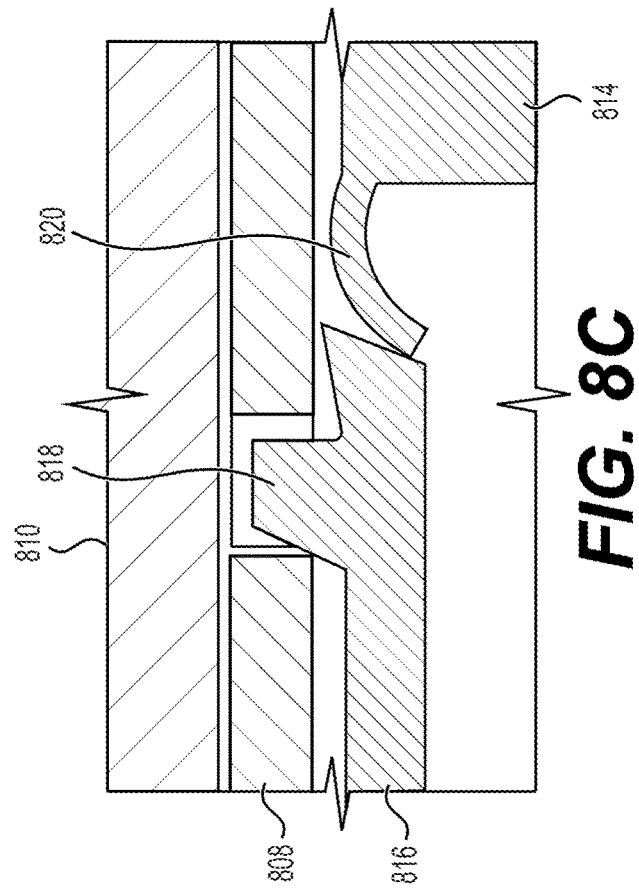

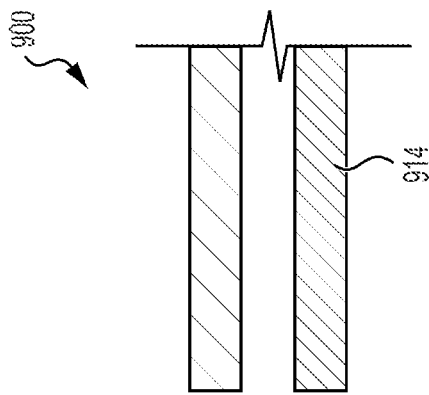
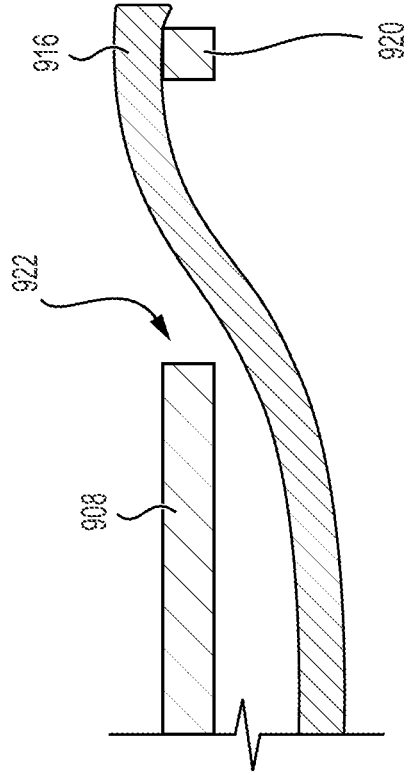
*FIG. 9A*
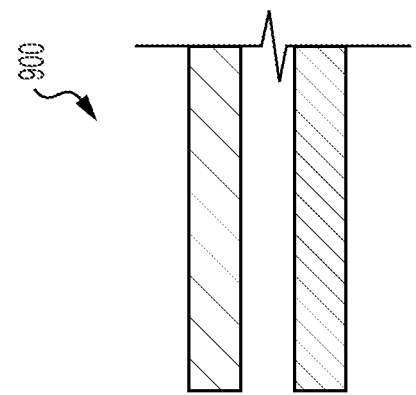
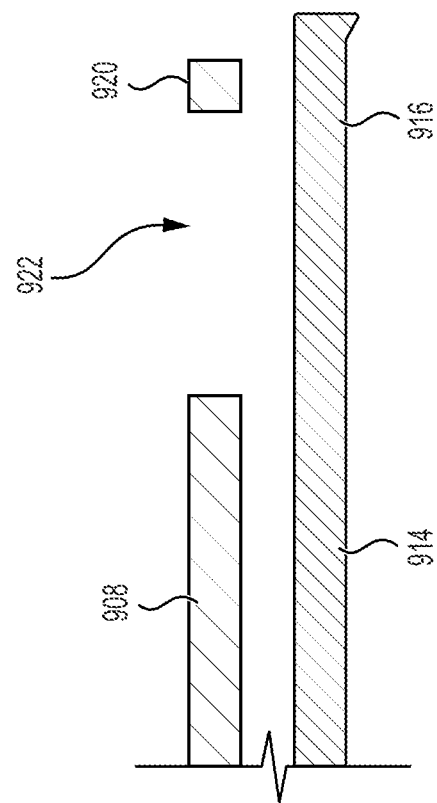
*FIG. 9B*

INJECTOR DEVICE

TECHNICAL FIELD

This application relates to an injector device for delivery of a medicament, particularly to an auto-injector device.

BACKGROUND

Injector devices are used to deliver a range of medicaments. In an auto-injector device, some or all of the actions required to use the injector device in administering medicament to a user are automated.

It is known to provide an auto-injector device having a needle cover which is axially movable to cover and uncover a needle, with the needle cover being biased by a spring to extend over the needle. Typically, the user presses the needle cover against an injection site, against the force of the spring, to push the needle cover into the housing and to uncover the needle which is pushed into the injection site. Medicament is automatically dispensed from the needle via an automated mechanism. A user typically holds the needle cover in a holding position for a predetermined period of time, to ensure that the correct dose of medicament is dispensed from the device, before removing the device from the injection site.

Some users find it difficult to fully depress the needle cover due to the force required or the change in force experienced during the activation movement. This may result in the needle not entering the user's skin to the correct depth, pain, discomfort, a wet injection site, early device removal and/or partial delivery of the medicament.

SUMMARY

A first aspect of this disclosure provides a medicament delivery device for reducing a force required to activate the medicament delivery device, wherein the medicament delivery device comprises:
  a needle for injecting medicament into a user, the needle disposed at a distal end of the medicament delivery device;
  a needle cover and a body, wherein the needle cover is axially movable relative to the body between an initial position, in which the needle cover covers the needle, and an activated position for dispensing medicament from the medicament delivery device, wherein in the activated position the needle protrudes from the distal end of the needle cover; and
  a carrier configured to support a pre-filled syringe, wherein the carrier is disposed within the needle cover and comprises a deformable element configured to change from a first configuration in which the deformable element is engaged with the needle cover to a second configuration in which the deformable element is not engaged with the needle cover.

The deformable element may have the first configuration when the needle cover is in the initial position and may have the second configuration when the needle cover is in an intermediate position, between the initial position and the activated position.

Movement of the needle cover from the initial position to the intermediate position may cause the deformable element to be deformed from the first configuration to the second configuration.

The needle cover may comprise a cooperating element and wherein the deformable element may be configured to engage with the cooperating element in the first configuration and to be disengaged from the cooperating element in the second configuration. The cooperating element may comprise an aperture, a recess, a ridge or a frictional surface. The cooperating element may comprises a slot and the deformable element is configured to abut an edge of the slot in the first configuration.

Movement of the needle cover proximally from the initial position may cause the deformable element to disengage from the slot.

The deformable element may be configured to produce a sound when deforming from the first configuration to the second configuration. The deformable element may be configured to produce a vibration when deforming from the first configuration to the second configuration.

The deformable element may be configured to be deformed from a first shape in the first configuration to a second shape in the second configuration. The deformable element may be configured:
  to have a convex shape which protrudes from the carrier towards the needle cover in the first configuration; and
  to have a concave shape which curves away from the needle cover in the second configuration.

The deformable element may be in a stressed state when in the second configuration.

The deformable element may be configured to be permanently retained in the second configuration by a latching member.

The deformable element may be configured to break in the second configuration. The deformable element may comprise a flexible arm with a stress concentrating region and may be configured to break at the stress concentrating region when the flexible arm is deflected by the needle cover.

The deformable element may be in a stressed state when in the first configuration.

The medicament delivery device of the first aspect may comprise multiple deformable elements.

The needle cover may comprise multiple cooperating elements and each of the multiple deformable elements may be configured to engage with a respective one of the multiple cooperating elements in the first configuration and to be disengaged from the respective cooperating element in the second configuration.

There may be a zero normal force between the deformable element and the needle cover when the deformable element has the second configuration.

The deformable element may comprise a flexible arm and a protrusion disposed on a free end of the flexible arm. A distal facing edge of the protrusion may be bevelled.

The medicament delivery device may further comprise a spring configured to exert a spring force which biases the needle cover axially, towards the distal end of the medicament delivery device.

The medicament delivery device may further comprise the pre-filled syringe.

A second aspect of this disclosure provides a medicament delivery device for reducing a force required to activate the medicament delivery device, wherein the medicament delivery device comprises:
  a needle for injecting medicament into a user, the needle disposed at a distal end of the medicament delivery device;
  a needle cover and a body, wherein the needle cover is configured to be moved in a proximal direction into the body of the medicament delivery device to expose the needle;

a pre-filled syringe carrier, wherein the pre-filled syringe carrier is disposed within the needle cover and comprises a deformable element, wherein the deformable element is configured:

prior to activation of the medicament delivery device, to have a first configuration in which the deformable element is engaged with the needle cover;

during an initial portion of an activation movement of the needle cover, to be forced to deform into a second configuration by movement of the needle cover, wherein the deformable element is not engaged with the needle cover when in the second configuration; and to remain in the second configuration for the remainder of the activation movement of the needle cover so as to reduce a force required to move the needle cover in a proximal direction into the body of the medicament delivery device.

The deformable element may deform permanently into the second configuration.

The deformable element may be configured to be deformed from a first shape in the first configuration to a second shape in the second configuration.

The deformable element may be configured: to have a convex shape which protrudes from the carrier towards the needle cover in the first configuration; an to have a concave shape which curves away from the needle cover in the second configuration.

The deformable element may be configured to be permanently retained in the second configuration by a latching member.

The deformable element may be in a stressed state when in the first configuration.

The deformable element may be configured to break in the second configuration.

BRIEF DESCRIPTION OF THE DRAWINGS

Reference is made to the accompanying drawings in which:

FIG. 1A shows an injector device with a cap attached;

FIG. 1B shows the injector device of FIG. 1A with the cap removed;

FIG. 3A shows a device in a pre-use state;

FIG. 3B shows the device at the start of an activation movement;

FIG. 5A shows a medicament delivery device according to a first embodiment in an initial state;

FIG. 5B shows the medicament delivery device of the first embodiment at the start of an activation movement;

FIG. 7A shows a medicament delivery device according to a second embodiment in an initial state;

FIG. 7B shows the medicament delivery device of the second embodiment at the start of an activation movement;

FIG. 7C shows the medicament delivery device of the second embodiment in an activated state;

FIG. 8A shows a medicament delivery device according to a third embodiment in an initial state;

FIG. 8B shows the medicament delivery device of the second embodiment in an activated state;

FIG. 8C shows a close-up of a deformable element of the third embodiment in a first configuration;

FIG. 8D shows a close-up of a deformable element of the third embodiment in a second configuration;

FIG. 9A shows portions of a medicament delivery device according to a fourth embodiment with a deformable element in a first configuration;

FIG. 9B shows portions of a medicament delivery device according to a fourth embodiment with a deformable element in a second configuration.

DETAILED DESCRIPTION

Figure 2B:
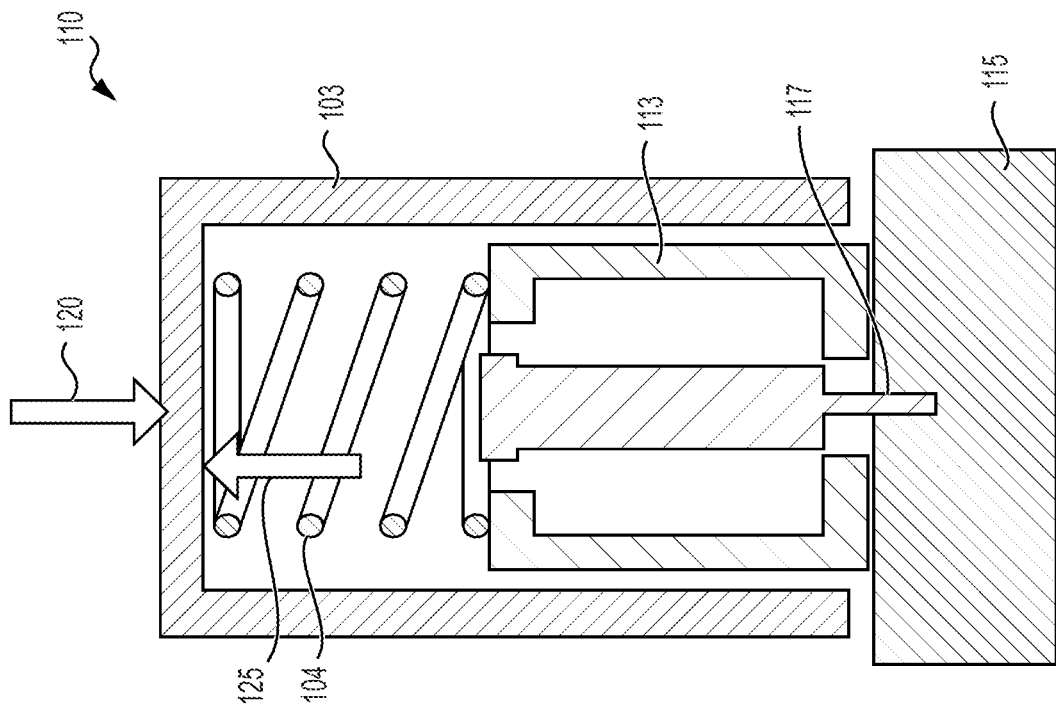
FIG. 2B shows a view of the device of FIG. 2A with injector device in the holding position.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user removes cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe to a more distal location within the syringe in order to force a medicament from the syringe through needle 17. In some embodiments, a drive spring is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring, located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2A:
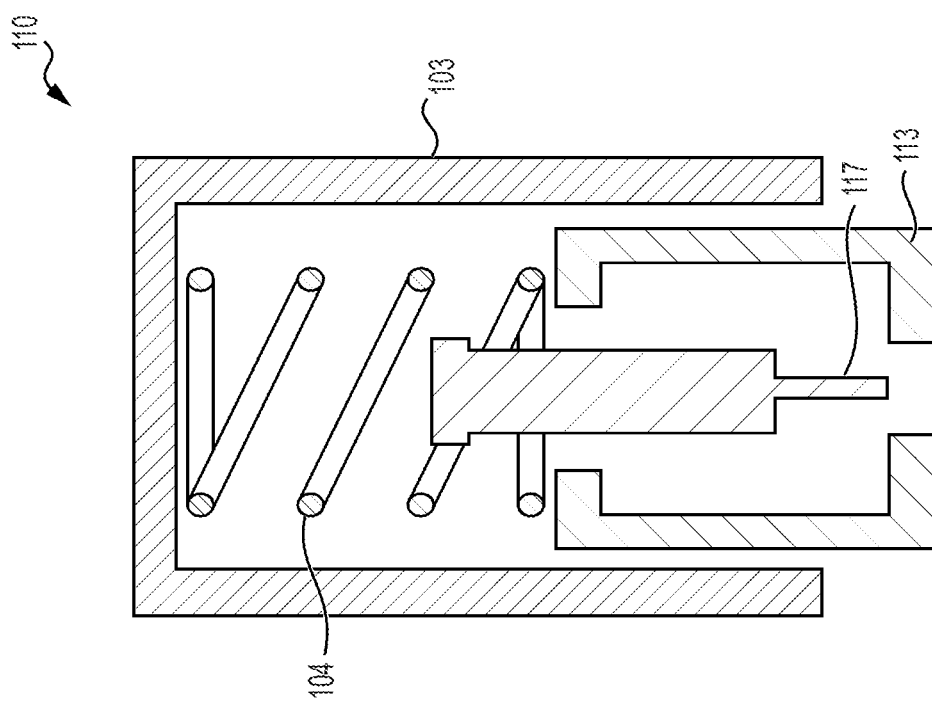
FIG. 2A shows a simplified view of an injector device prior to use.

FIGS. 2A and 2B show a simplified view of a device 110 having a needle cover 113 which is axially movable to cover and uncover the needle 117. The needle cover 113 is biased by a spring 104 to extend over the needle 117.

FIG. 2A shows the device before use, in which the needle cover 113 is exposed out of the end of the device body 103 and covers the needle 117. A force can be applied by a user against a spring force 125 to move the needle cover 113 from the position shown in FIG. 2A towards a holding position shown in FIG. 2B, and a holding force 120 can be applied to maintain the needle cover in the holding position.

Typically the user presses the needle cover 113 against an injection site 115 to push the needle cover 113 at least partially into the device body 103. The exposed needle 117 is pushed into the injection site 115. In the holding position, medicament is automatically dispensed from the needle 117 via an automated mechanism. A user typically holds the needle cover 113 in the holding position for a predetermined period of time, to ensure that the correct dose of medicament is dispensed from the device 110, before removing the device from the injection site 115.

The spring force 125 against which the user must applies a force to move the needle cover 113 is one component of the "activation force" of the device 110. The activation force refers to the force or force profile that the user exerts on the device 110 to move the needle cover 113 from the position shown in FIG. 2A to the position shown in FIG. 2B. If this force or force profile is not well balanced, it can lead to difficulty in activating the device 100 for some users, or increase the pain or anxiety associated with using the device.

FIGS. 3A to 3D show further details of the operation of the device 110. These Figures each show a cross section of the one half of the device 110 during various stages of activation of the device.

FIG. 3A shows the device in a pre-use state, may also be called an initial state or initial position. The needle cover 113 covers the needle 117 in this position. A spring may bias the needle cover 113 distally so that it extends over the needle 117. The device 110 also comprises a carrier 300, which supports a pre-filled syringe 302. The needle 117 is in fluid communication with the pre-filled syringe 302 and extends from the distal end of the pre-filled syringe 302. The carrier 300 comprises a resilient member 304 which takes the form of a flexible arm which extends axially (or longitudinally) and which has a protrusion 306 on the free end of the flexible arm. The protrusion 306 extends radially from the flexible arm to engage with a first slot in the needle cover 113.

Although one resilient member 304 is shown in FIG. 3A, the carrier 300 may comprise two or more resilient members 304. For example, two resilient members 304 may be disposed opposite each other on the carrier 300 and may engage with corresponding slots in the needle cover 113. Having the resilient member 304 engage a slot in the needle cover 113 in this initial position may prevent axial travel of the needle cover 113 during assembly of the device 110 and may help to prevent inadvertent activation of the device 110.

FIG. 3B shows the device 110 at the start of an activation movement. A distal force is applied via the body 103 while the needle cover 113 is placed against the user's skin, causing the needle cover 113 to move proximally into the device 110. During this initial movement, the resilient member 304 is deflected and exits the first slot in the needle cover 113. The resilient member 304 abuts an inner surface of the needle cover 113 resulting in a normal force between these components. This leads to a frictional force which resists proximal movement of the needle cover 113 into the device 110 and therefore increases the force required to activate the device 110.

Figure 3C:
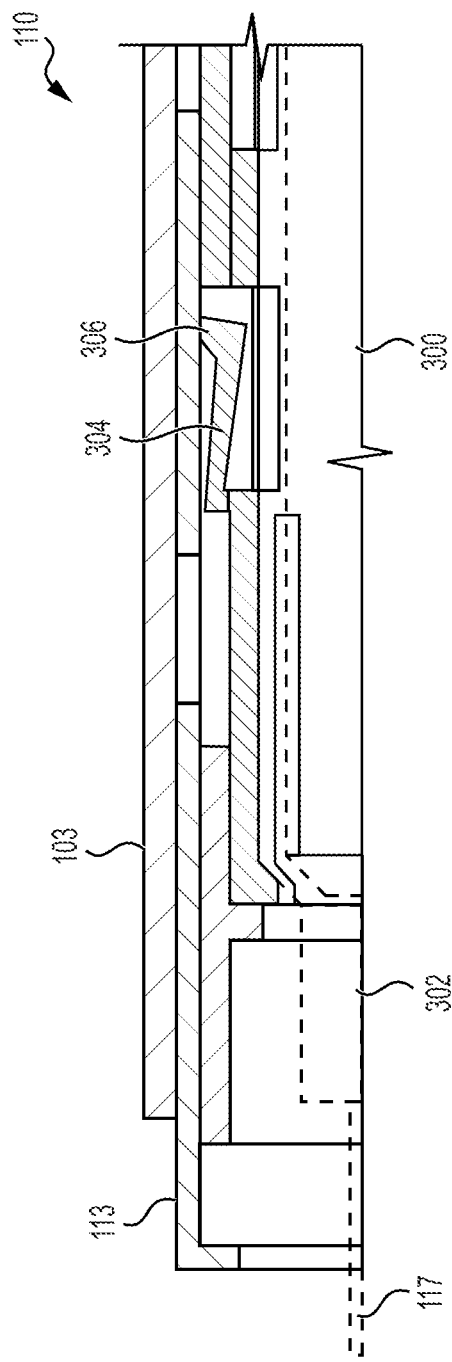
FIG. 3C shows the device in a mid-activation state.

FIG. 3C shows the device 110 in a mid-activation state. In this position, the needle 117 has protruded from the end of the needle cover 113, but the medicament dispensing mechanism of the device 110 has not yet been triggered. As can be seen, the resilient member 304 is still in a deflected state and still exerts and normal and frictional force on the needle cover 113.

Figure 3D:
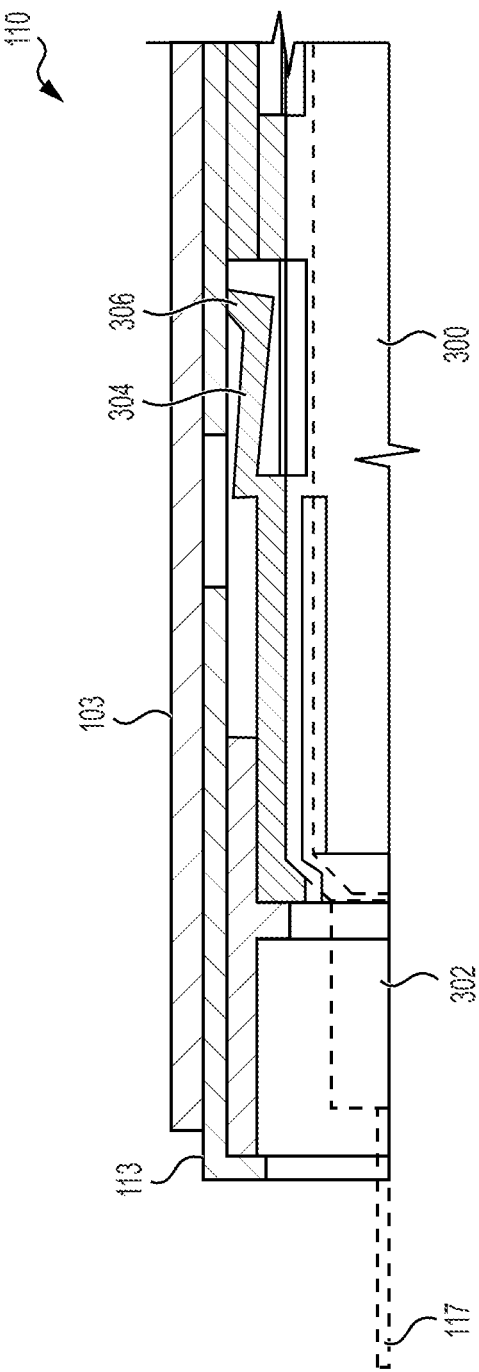
FIG. 3D shows the device in an activated state.

FIG. 3D shows the device 110 in an activated state. In this position the needle cover 113 is fully displaced into the device 110, the needle 117 protrudes from the end of the needle cover 113 to its maximum extend and the medicament dispensing mechanism of the device 110 is triggered. As can be seen, the resilient member 304 is still in a deflected state and still exerts and normal and frictional force on the needle cover 113.

After the medicament has been delivered, during removal of the device 110, the sequence of FIGS. 3A to 3D is reversed. The resilient member 304 remains in a deflected state until the needle cover 113 returns to the initial position.

Figure 4A:
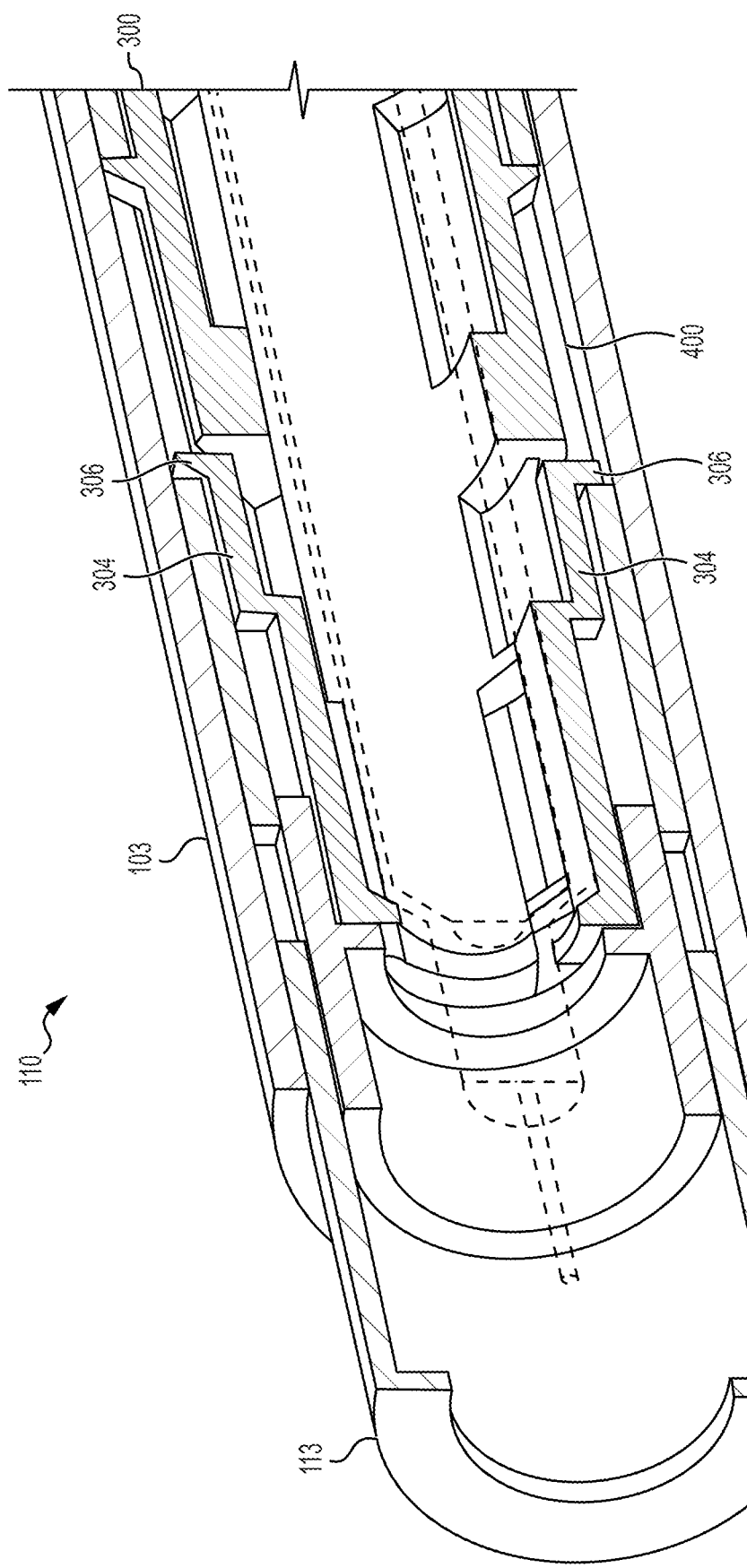
FIG. 4A is a perspective view of a cross section of the device in the initial state of FIG. 3A.

FIG. 4A is a perspective view of a cross section of the device 110 in the initial state (as also shown in FIG. 3A). In this view it can be seen that the protrusion 306 of the resilient member 304 abuts an end face of the slot 400 in the needle cover 113. The carrier 300 comprises two resilient members 304 on opposite sides and there are two corresponding slots 400 in the needle cover 113.

Figure 4B:
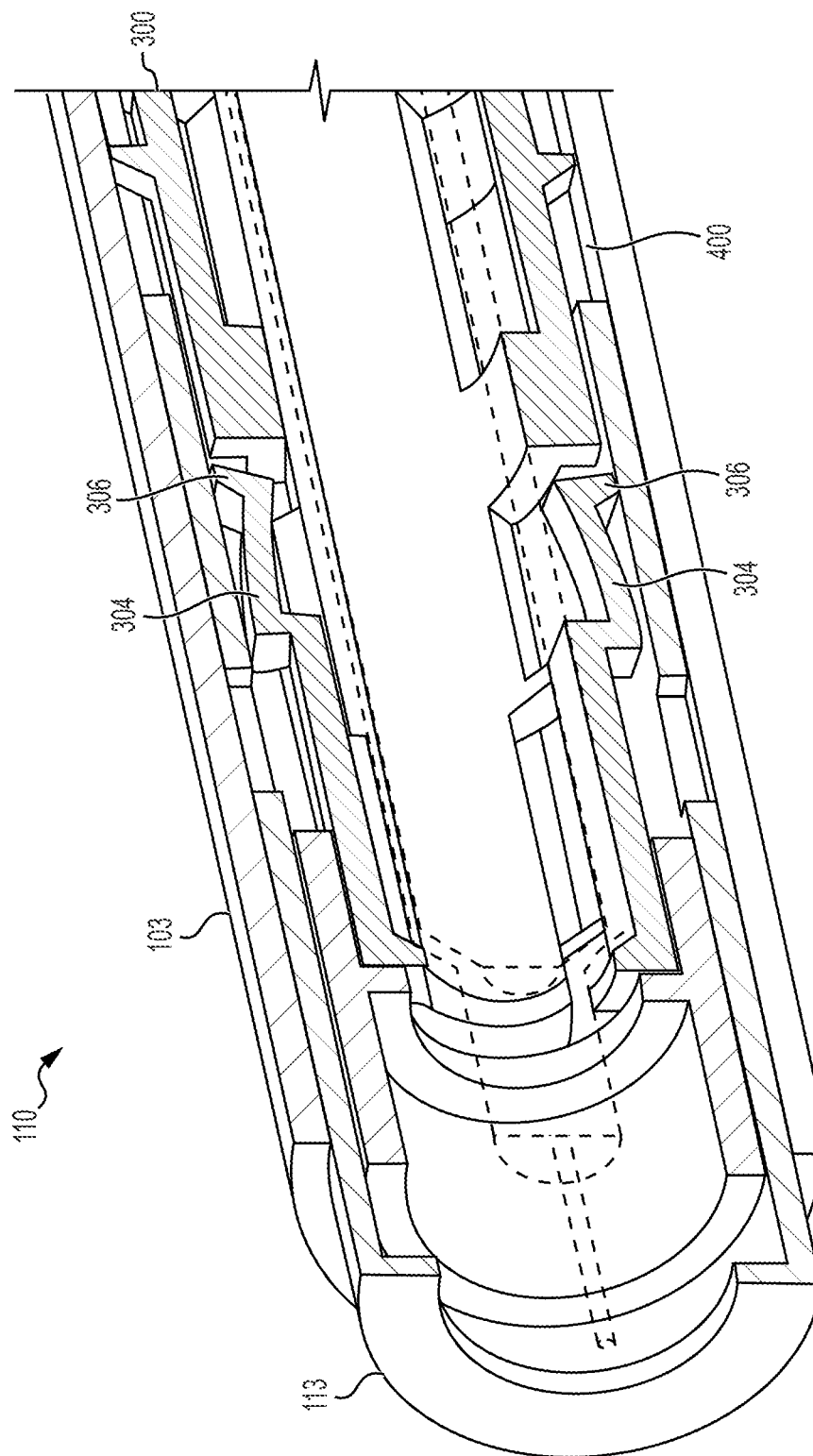
FIG. 4B is a perspective view of a cross section of the device in the mid-activation state of FIG. 3C.

FIG. 4B is a perspective view of a cross section of the device 110 in a mid-activation state (as also shown in FIG. 3C). In this view it can be seen that the resilient members 304 are deflected, so that the protrusions 306 on the free ends of the flexible arms contact the inner surface of the needle cover 113, increasing the force needed to move the needle cover 113 proximally with respect to the body 103 of the device 110.

Figure 5C:
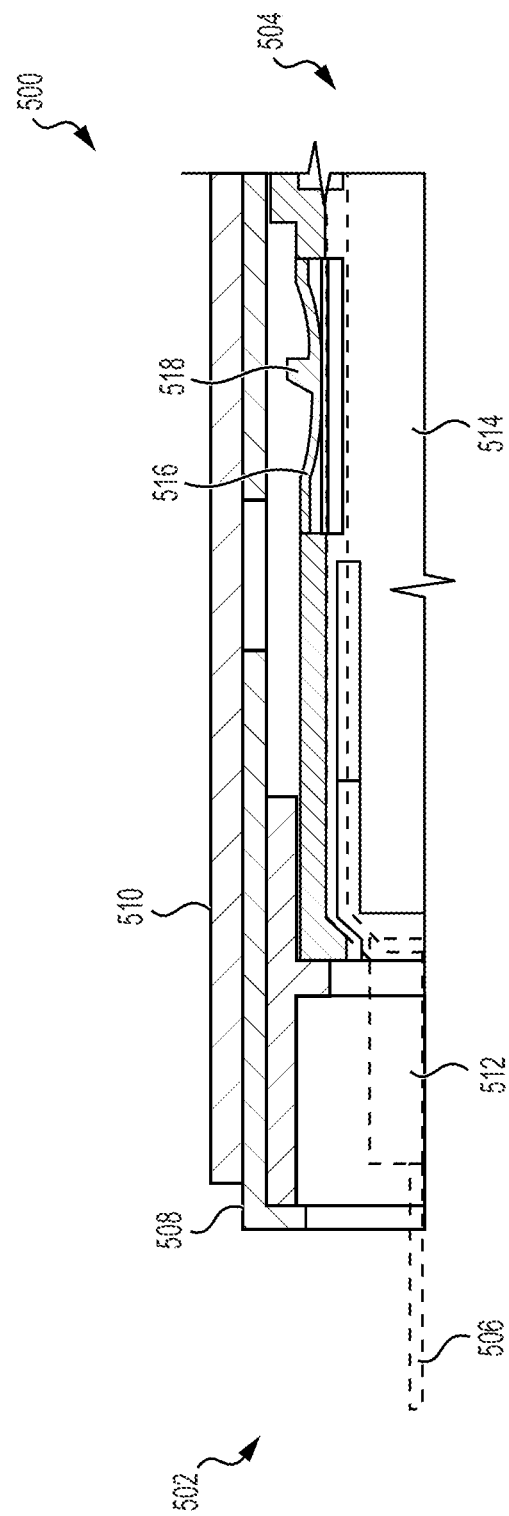
FIG. 5C shows the medicament delivery device of the first embodiment in an activated state.

FIGS. 5A to 5C shows features of a first embodiment of a medicament delivery device 500, which is also referred to herein as an injector device. These Figures each show a cross section of the one half of the device 500 during various stages of activation of the device.

The device has a distal end 502 and a proximal end 504. The device 500 has a needle 506 for injecting medicament into a user at an injection site, a needle cover 508 and a body 510. The body 510 is configured to be gripped by a user. The body 510 forms part of the external surface of the device. The device 500 houses a pre-filled syringe 512. The needle 506 is in fluid communication with the pre-filled syringe 512 and extends from the distal end of the pre-filled syringe 512. The needle cover 508 is axially movable relative to the body 510 between an initial position, shown in FIG. 5A, in which the needle cover 508 covers the needle 506, and an activated position, shown in FIG. 5C, for dispensing medicament from the device. In the activated position, the needle 506 protrudes from the distal end of the needle cover 508.

A spring may exert a spring force against the needle cover 508 which biases the needle cover axially, in the distal direction. A force can be applied by a user against the force of the spring to move the needle cover 508 from the position shown in FIG. 5A towards the position shown in FIG. 5C.

Medicament is dispensed from the medicament delivery device 500 via the needle 506 while the needle cover 508 is in the activated position. An automated mechanism is triggered to start the dispensing of medicament when the needle cover 508 reaches a predetermined axial position within the housing. The predetermined position is located just distally of the activated position. The automated mechanism may comprise a plunger which is automatically released when the needle cover 508 reaches the predetermined axial position. When the plunger is released it moves within the pre-filled syringe to dispense medicament from the syringe through the needle 506.

Typically the user removes a cap from the distal end of the medicament delivery device 500. The user presses the needle cover 508 against an injection site to move the needle cover 508 axially relative to the body 510 and to uncover the needle 506. The needle 506 is pushed into the injection site. The automated mechanism is released, and medicament is automatically dispensed from the device via the needle 506. The user holds the needle cover 508 in the activated position while the medicament is dispensed.

FIG. 5A shows the device 500 in a pre-use state, which may also be called an initial state or initial position. The needle cover 508 covers the needle 506 in this position. The device 500 also comprises a carrier 514, which supports the pre-filled syringe 512. The carrier 514 comprises a deformable element 516 which takes the form of a flexible component. FIG. 5A shows the deformable element 516 in a first configuration in which it has a convex shape which protrudes from the carrier 514 towards the needle cover 208. The deformable element 516 comprises a protrusion 518 disposed on the flexible member. The protrusion 518 may be positioned approximately in the centre of the flexible member and directed towards the carrier 514. The flexible member may be an extruded piece of the body of the carrier or a separate element, secured at both ends to the body of the carrier 514.

The deformable element 516 may be stressed when in the first configuration. For example, some compression or tension forces may be present in the flexible member. Alternatively, the deformable element 516 may be in a relaxed state in the first configuration.

The needle cover has a cooperating element, which may take the form of an aperture, a recess, a ridge or a frictional surface. The deformable element 516 is configured to engage with the cooperating element while in the first configuration and thereby to provide a resistance to proximal movement of the needle cover 508 relative to the carrier 514 and body 510. In this embodiment, the cooperating element has the form of a slot (see FIGS. 6A and 6B) and the deformable element is configured to abut an edge of the slot in the first configuration. The protrusion 518 of the deformable element 516 may abut a proximally facing edge of the slot. A distal facing edge of the protrusion 518 may be beveled, to allow the protrusion 518 to be forced radially inwards when the needle covers is pushed proximally.

Although one deformable element 516 is shown in FIG. 5A, the carrier 514 may comprise two or more deformable elements 516. For example, two deformable elements 516 may be disposed opposite each other on the carrier 514 and may engage with corresponding slots in the needle cover 508.

FIG. 5B shows the device 500 at the start of an activation movement. A distal force is applied via the body 510 while the needle cover 508 is placed against the user's skin, causing the needle cover 508 to move proximally into the device 500. In this position, the needle cover 508 is in an intermediate position, between the initial position and the activated position.

During this initial movement, the deformable element 516 is deflected and exits the slot in the needle cover 508. In particular a normal force is exerted on the protrusion 518 which is forced radially inwards. This causes the flexible member to bend downwards or to become less convex. As the main body of the carrier 514 is rigid, compression forces build in the deformable element 516. When the deformable element 516 has deflected past a critical position, e.g. beyond a position parallel with the fixed end points of the flexible member, then it snaps into a second configuration, as shown in FIG. 5B. In this manner, movement of the needle cover 508 from the initial position to the intermediate position causes the deformable element 516 to be deformed from the first configuration to the second configuration. In the second configuration, the deformable element 516 has a concave shape which curves away from the needle cover 508. Thus the deformable element 516 deforms from a first shape in the first configuration to a second shape in the second configuration.

The carrier 514 may have an aperture or recess underneath the deformable element 516 to allow room for it to deform into the concave shape. The deformable element 516 may be stressed when in the second configuration. For example, some compression or tension forces may be present in the flexible member. Alternatively, the deformable element 516 may be in a relaxed state in the second configuration.

The deformable element 516 may produce a sound when deforming from the first configuration to the second configuration, for example a snapping sound. This may be used to provide feedback to a user or to a sensor within the device 500 or attached to the device 500. The snap sound may be produced by the deformable element 516 itself, or by the deformable element 516 striking an inner surface of a recess in the carrier 514 as it transitions to the second shape.

Alternatively, or in addition, the deformable element 516 may be configured to produce a vibration when deforming from the first configuration to the second configuration. Again, this may be used to provide feedback to a user or to a sensor within the device 500 or attached to the device 500. The vibration may be produced by the deformable element 516 itself, or by the deformable element 516 striking an inner surface of a recess in the carrier 514 as it transitions to the second shape.

The deformable element 516 may be referred to as a permanently deformable element or irreversibly deformable element, since in some examples after the element is deformed, the deformation cannot be reversed. In this embodiment, the deformable element 516 does not again assume a convex shape.

FIG. 5C shows the device 500 in an activated state. In this position the needle cover 508 is fully displaced into the device 500 and is in an activated position. The needle 506 protrudes from the end of the needle cover 508 to its maximum extend and the medicament dispensing mechanism of the device 500 is triggered. As can be seen, the deformable element 516 remains in the second configuration. Thus the deformable element 516 does not exert any normal or friction force on the needle cover 508 in this position or at any point after the intermediate position. The activation force on the needle cover 508 required after the intermediate position is reached is therefore reduced compared to other devices.

After the medicament has been delivered, during removal of the device 500, the movement of the needle cover 508 is reversed, but the deformable element 516 remains in its second configuration.

Figure 6A:
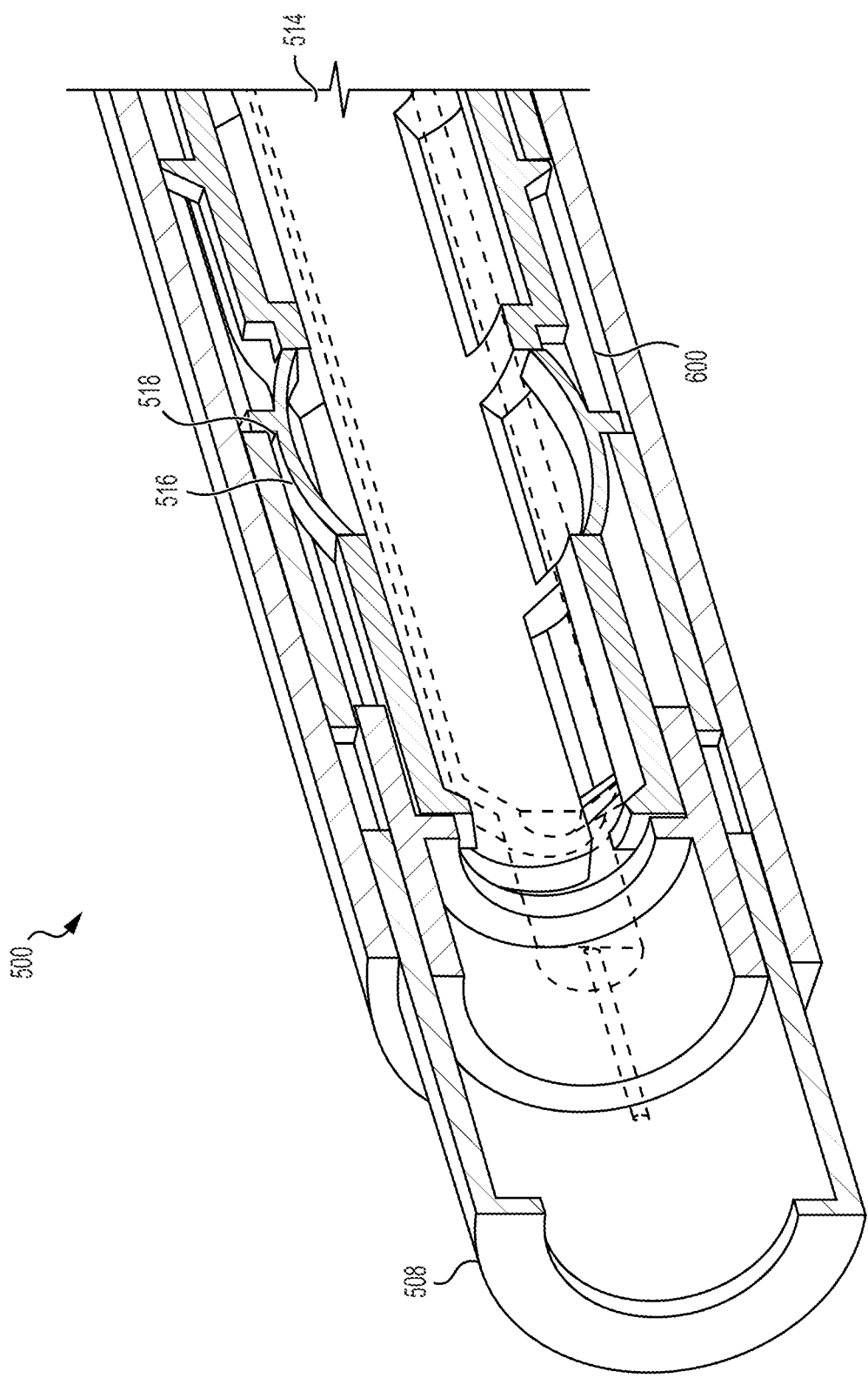
FIG. 6A is a perspective view of a cross section of the medicament delivery device of the first embodiment in the initial state of FIG. 5A.

FIG. 6A is a perspective view of a cross section of the device 500 in the initial state (as also shown in FIG. 5A). In this Figure, the needle cover 508 is in the initial position. It can be seen that the deformable element 516 has a convex shape and a protrusion 518 of the deformable element 516 abuts a proximally facing end face of a slot 600 in the needle cover 508. The slot 600 extends axially and is an aperture through the wall of the needle cover 508. In some other embodiments, the slot 600 may be provided as a recess in the inner surface of the needle cover 508, which does not extend completely through the wall of the needle cover 508, but which is deep enough to accommodate the protrusion 518 of the deformable element 516 in the first configuration.

Figure 6B:
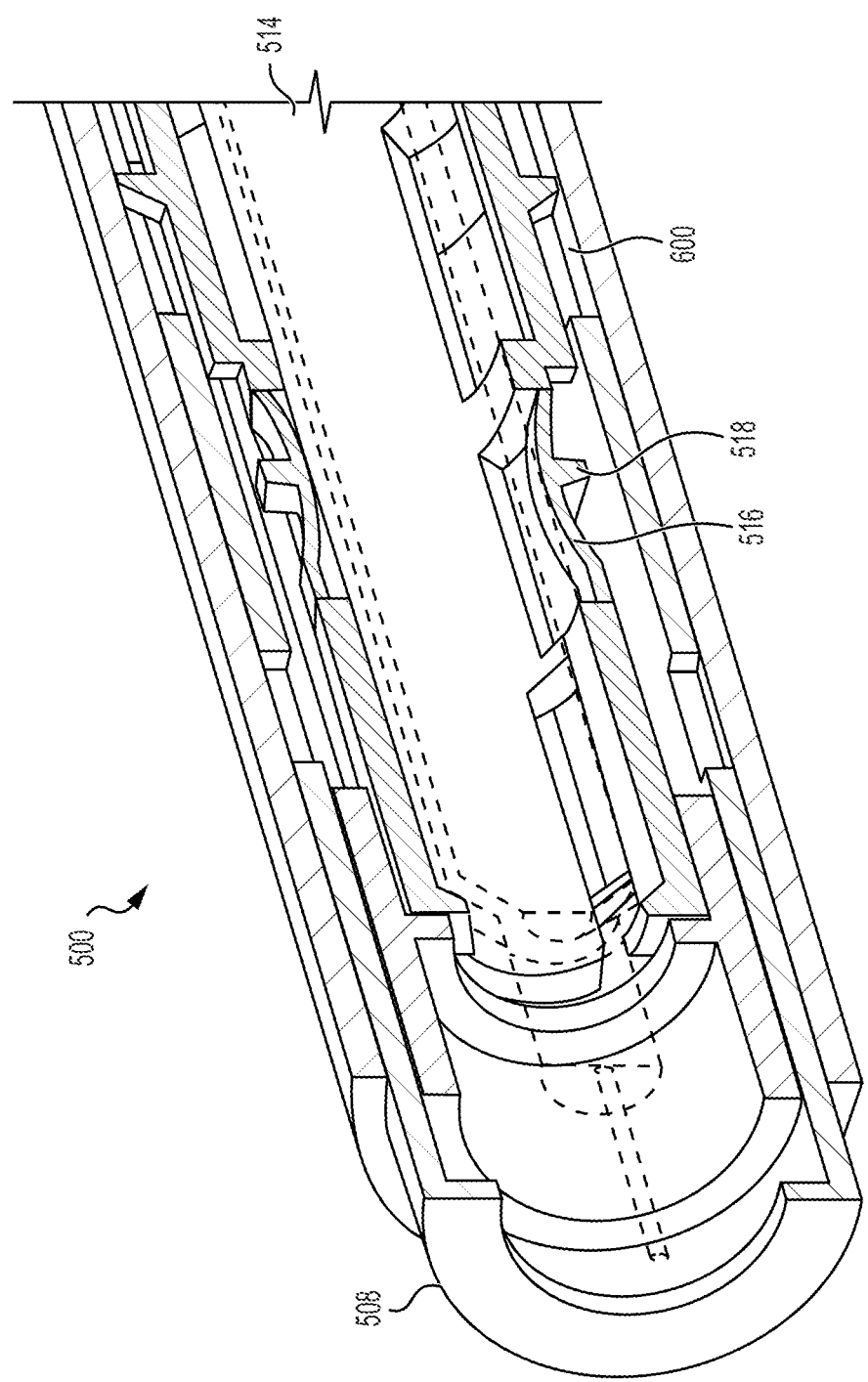
FIG. 6B is a perspective view of a cross section of the medicament delivery device of the first embodiment at the start of an activation movement (equivalent to FIG. 5B)

FIG. 6B is a perspective view of a cross section of the device 500 at the start of an activation movement (as also shown in FIG. 5B). In this position, the needle cover 508 has moved proximally to an intermediate position and the needle 506 is still shielded by the needle cover 508. The medicament dispensing mechanism of the device 500 has not yet been triggered.

In this intermediate position, the deformable element 516 has a convex shape and is in a second configuration. The deformable element 516 remains in this second configuration for the remainder of the activation movement and throughout device removal. No part of the deformable element 516 is in contact with the needle cover 508 and thus the deformable element 516 does not exert any normal or friction force on the needle cover 508 in this position.

In the embodiment depicted, the carrier 514 comprises two deformable elements 516 on opposite sides and there are two corresponding slots 600 in the needle cover 508. In general, a symmetrical arrangement of deformable elements 516 may help to ensure a consistent force profile when the device 500 is used.

FIGS. 7A to 7C shows features of a second embodiment of a medicament delivery device 700, which is also referred to herein as an injector device. These Figures each show a cross section of the one half of the device 700 during various stages of activation of the device.

The device has a distal end 702 and a proximal end 704. The device 700 has a needle 706 for injecting medicament into a user at an injection site, a needle cover 708 and a body 710. The body 710 is configured to be gripped by a user. The body 710 forms part of the external surface of the device. The device 700 houses a pre-filled syringe 712. The needle 706 is in fluid communication with the pre-filled syringe 712 and extends from the distal end of the pre-filled syringe 712. The needle cover 708 is axially movable relative to the body 710 between an initial position, shown in FIG. 7A, in which the needle cover 708 covers the needle 706, and an activated position, shown in FIG. 7C, for dispensing medicament from the device. In the activated position, the needle 706 protrudes from the distal end of the needle cover 708.

A spring may exert a spring force against the needle cover 708 which biases the needle cover axially, in the distal direction. A force can be applied by a user against the force of the spring to move the needle cover 708 from the position shown in FIG. 7A towards the position shown in FIG. 7C.

Medicament is dispensed from the medicament delivery device 700 via the needle 706 while the needle cover 708 is in the activated position. An automated mechanism is triggered to start the dispensing of medicament when the needle cover 708 reaches a predetermined axial position within the housing. The predetermined position is located just distally of the activated position. The automated mechanism may comprise a plunger which is automatically released when the needle cover 708 reaches the predetermined axial position. When the plunger is released it moves within the pre-filled syringe to dispense medicament from the syringe through the needle 706.

Typically the user removes a cap from the distal end of the medicament delivery device 700. The user presses the needle cover 708 against an injection site to move the needle cover 708 axially relative to the body 710 and to uncover the needle 706. The needle 706 is pushed into the injection site. The automated mechanism is released, and medicament is automatically dispensed from the device via the needle 706. The user holds the needle cover 708 in the activated position while the medicament is dispensed.

FIG. 7A shows the device 700 in a pre-use state, which may also be called an initial state or initial position. The needle cover 708 covers the needle 706 in this position. The device 700 also comprises a carrier 714, which supports the pre-filled syringe 712. The carrier 714 comprises a deformable element 716 which takes the form of a flexible arm. The flexible arm may be an extruded piece of the body of the carrier or a separate element, secured at one end to the body of the carrier 714. The free end of the arm comprises a protrusion 718 directed towards the carrier 714.

FIG. 7A shows the deformable element 716 in a first configuration in which it is engaged with a cooperating element of the needle cover 708. The cooperating element may take the form of an aperture, a recess, a ridge or a frictional surface. The deformable element 716 is configured to engage with the cooperating element while in the first configuration and thereby to provide a resistance to proximal movement of the needle cover 708 relative to the carrier 714 and body 710. In this embodiment, the cooperating element has the form of a slot and the deformable element is configured to abut an edge of the slot in the first configuration. The protrusion 718 of the deformable element 716 may abut a proximally facing edge of the slot. A distal facing edge of the protrusion 718 may be beveled, to allow the protrusion 718 to be forced radially inwards when the needle covers is pushed proximally.

The deformable element 716 has a stress concentrating region 720. The stress concentrating region 720 may be located approximately half-way between the fixed and free ends of the flexible arm. The stress concentrating region 720 may comprise a thinned or weakened area of the flexible arm. The deformable element 716 may be in a relaxed state in the first configuration.

Although one deformable element 716 is shown in FIG. 7A, the carrier 714 may comprise two or more deformable elements 716. For example, two deformable elements 716 may be disposed opposite each other on the carrier 714 and may engage with corresponding slots in the needle cover 708.

FIG. 7B shows the device 700 at the start of an activation movement. A distal force is applied via the body 710 while the needle cover 708 is placed against the user's skin, causing the needle cover 708 to move proximally into the device 700. In this position, the needle cover 708 is in between the initial position and the activated position.

During this initial movement, the deformable element 716 is deflected and exits the slot in the needle cover 708. In particular a normal force is exerted on the protrusion 718 which is forced radially inwards. This causes the flexible arm to bend downwards and be put under stress.

When the deformable element 716 is deflected past a critical position, e.g. coinciding with the amount of deflection produced by exiting the slot in the needle cover 708, the stress in the stress concentrating region causes the deformable element 716 to break, as shown in FIG. 7C. In this manner, movement of the needle cover 708 from the initial position to an intermediate position causes the deformable element 716 to be deformed from the first configuration to the second configuration. In the second configuration, the deformable element 716 has broken. FIG. 7C shows the device 700 in an activated state. However, the deformable element 716 may be configured to break before the needle cover 708 reaches the activated position. For example, the deformable element 716 may break as soon as, or shortly after, the protrusion 718 of the flexible arm exits the slot in the needle cover 708.

The deformable element 716 may be configured to break entirely into two pieces. The carrier 714 may have an aperture or recess underneath the deformable element 716 to allow room for the broken end piece of the deformable element 716 to be accommodated.

The deformable element 716 may produce a sound when deforming from the first configuration to the second configuration, for example a snapping sound. This may be used to provide feedback to a user or to a sensor within the device 700 or attached to the device 700. The snap sound may be produced by the deformable element 716 itself when it breaks.

Alternatively, or in addition, the deformable element 716 may be configured to produce a vibration when deforming from the first configuration to the second configuration. Again, this may be used to provide feedback to a user or to a sensor within the device 700 or attached to the device 700. The vibration may be produced by the deformable element 716 itself when breaking.

The deformable element 716 may be referred to as a permanently deformable element or irreversibly deformable element, since after the element is deformed, the deformation cannot be reversed. In this embodiment, after it is broken, the deformable element 716 does not exert a force on the needle cover for the remainder of its movement or during device removal. The activation force on the needle cover 708 required after the intermediate position is reached is therefore reduced compared to prior art devices.

After the medicament has been delivered, during removal of the device 700, the movement of the needle cover 708 is reversed, but the deformable element 716 remains in its second configuration.

FIGS. 8A to 8D shows features of a third embodiment of a medicament delivery device 800, which is also referred to herein as an injector device. These Figures each show a cross section of the device 800 or a part of the device 800 during various stages of activation of the device.

The device has a distal end 802 and a proximal end 804. The device 800 has a needle 806 for injecting medicament into a user at an injection site, a needle cover 808 and a body 810. The body 810 is configured to be gripped by a user. The body 810 forms part of the external surface of the device. The device 800 houses a pre-filled syringe 812. The needle 806 is in fluid communication with the pre-filled syringe 812 and extends from the distal end of the pre-filled syringe 812. The needle cover 808 is axially movable relative to the body 810 between an initial position, shown in FIG. 8A, in which the needle cover 808 covers the needle 806, and an activated position, shown in FIG. 8C, for dispensing medicament from the device. In the activated position, the needle 806 protrudes from the distal end of the needle cover 808.

A spring may exert a spring force against the needle cover 808 which biases the needle cover axially, in the distal direction. A force can be applied by a user against the force of the spring to move the needle cover 808 from the position shown in FIG. 8A towards the position shown in FIG. 8B.

Medicament is dispensed from the medicament delivery device 800 via the needle 806 while the needle cover 808 is in the activated position. An automated mechanism is triggered to start the dispensing of medicament when the needle cover 808 reaches a predetermined axial position within the housing. The predetermined position is located just distally of the activated position. The automated mechanism may comprise a plunger which is automatically released when the needle cover 808 reaches the predetermined axial position. When the plunger is released it moves within the pre-filled syringe to dispense medicament from the syringe through the needle 806.

Typically the user removes a cap from the distal end of the medicament delivery device 800. The user presses the needle cover 808 against an injection site to move the needle cover 808 axially relative to the body 810 and to uncover the needle 806. The needle 806 is pushed into the injection site. The automated mechanism is released, and medicament is automatically dispensed from the device via the needle 806. The user holds the needle cover 808 in the activated position while the medicament is dispensed.

FIG. 8A shows the device 800 in a pre-use state, which may also be called an initial state or initial position. The needle cover 808 covers the needle 806 in this position. The device 800 also comprises a carrier 814, which supports the pre-filled syringe 812. The carrier 814 comprises a deformable element 816 which takes the form of a flexible arm. The flexible arm may be an extruded piece of the body of the carrier or a separate element, secured at one end to the body of the carrier 814. The free end of the arm comprises a protrusion 818 directed towards the carrier 814.

FIG. 8A shows the deformable element 816 in a first configuration in which it is engaged with a cooperating element of the needle cover 808. The cooperating element may take the form of an aperture, a recess, a ridge or a frictional surface. The deformable element 816 is configured to engage with the cooperating element while in the first configuration and thereby to provide a resistance to proximal movement of the needle cover 808 relative to the carrier 814 and body 810. In this embodiment, the cooperating element has the form of a slot and the deformable element is configured to abut an edge of the slot in the first configuration. The protrusion 818 of the deformable element 816 may abut a proximally facing edge of the slot. A distal facing edge of the protrusion 818 may be beveled, to allow the protrusion 818 to be forced radially inwards when the needle covers is pushed proximally.

The carrier 814 also comprises a latching member 820. The latching member 820 may comprise a flexible projection which extends distally form a portion of the carrier 814 and has a free end which contacts an underside or beveled end face of the deformable element 816, which may hold it in the first configuration.

Although one deformable element 816 is shown in FIG. 8A, the carrier 814 may comprise two or more deformable elements 816. For example, two deformable elements 816 may be disposed opposite each other on the carrier 814 and may engage with corresponding slots in the needle cover 808.

FIG. 8C shows a close-up of the free end of the deformable element 816 and the latching member 820 in the first configuration.

FIG. 8B shows the device 800 in an activated position. A distal force is applied via the body 810 while the needle cover 808 is placed against the user's skin, causing the needle cover 808 to move proximally into the device 800. The needle cover 808 thus enters a position between the initial position and the activated position. During this initial movement, the deformable element 816 is deflected and exits the slot in the needle cover 808. In particular a normal force is exerted on the protrusion 818 which is forced radially inwards. This causes the flexible arm to bend downwards and to overcome the resisting force of the latching member 820. The latching member 820 may bend downwards under the force exerted by the deformable element 816 until the free end of the latching member 820 clears the free end of the deformable element 816. At this point the latching member 820 snaps back up and abuts a top side of the deformable element 816. In this manner, movement of the needle cover 808 from the initial position to an intermediate position causes the deformable element 816 to be deformed from the first configuration to the second configuration.

FIG. 8B shows the device 800 in an activated state. However, the latching member 820 may be configured to clear the free end of the deformable element 816 before the needle cover 808 reaches the activated position. For example, latching member 820 may clear the free end of the deformable element 816 as soon as, or shortly after, the protrusion 818 of the flexible arm exits the slot in the needle cover 808.

The deformable element 816 may be in a relaxed state in the first configuration and a stressed state in the second configuration. The latching member 820 may be biased downwards (towards the center axis of the device 800). It may therefore exert a force on the top side of the deformable element 816 to maintain it in the second configuration. Alternatively, the deformable element 816 may be biased towards the second configuration. Thus, in the first configuration, the deformable element 816 is held in a stressed state by the latching member 820. The latching member 820 may still exert some downward biasing force on the top side of the deformable element 816 in the second configuration to ensure that no element contacts the needle cover 808 for the remainder of the activation movement.

The carrier 814 may have an aperture or recess underneath the deformable element 816 to allow room for it to deform into the second configuration.

The deformable element 816 and/or the latching member 820 may produce a sound when the deformable element 816 deforms from the first configuration to the second configuration, for example a snapping sound. This may be used to provide feedback to a user or to a sensor within the device 800 or attached to the device 800. The snap sound may be produced by the free end of the latching member 820 striking the protrusion 818 of the deformable element 816 or some other part of the free end of the deformable element 816.

Alternatively, or in addition, the deformable element 816 may be configured to produce a vibration when deforming from the first configuration to the second configuration. Again, this may be used to provide feedback to a user or to a sensor within the device 800 or attached to the device 800. The vibration may be produced by the free end of the latching member 820 striking the protrusion 818 of the deformable element 816 or some other part of the free end of the deformable element 816.

The deformable element 816 may be referred to as a permanently deformable element or irreversibly deformable element, since after the element is deformed, the deformation cannot be reversed. The deformable element 816 is either biased towards the second configuration or is restrained in the second configuration by the latching member 820, or both. The activation force on the needle cover 808 required after the intermediate position is reached is therefore reduced compared to other devices.

FIG. 8D shows a close-up of the free end of the deformable element 816 and the latching member 820 in the second configuration.

After the medicament has been delivered, during removal of the device 800, the movement of the needle cover 808 is reversed, but the deformable element 816 remains in its second configuration.

FIGS. 9A and 9B shows features of a fourth embodiment of a medicament delivery device 900, which is also referred to herein as an injector device. These Figures each show a cross section of a portion of a needle cover 908 and a carrier 914.

FIG. 9A shows a close up of a portion of the carrier 914 with a deformable element 916 and the region of the needle cover 908 with which it interacts. The other parts of the medicament delivery device 900 may be the same as those shown and described in the preceding embodiments.

FIG. 9A shows the device 900 in a pre-use state, which may also be called an initial state or initial position. The needle cover 908 covers the needle in this position. The deformable element 916 takes the form of a flexible arm. The flexible arm may be an extruded piece of the body of the carrier or a separate element, secured at one end to the body of the carrier 914. The free end of the arm may comprise a shaped portion which may be slightly larger in cross section than the reminder of the flexible arm.

The needle cover 908 has at least one slot 922 and a ledge feature 920 located within the slot 922 or at one end of the slot. FIG. 9A shows the deformable element 916 in a first configuration in which it is engaged with the ledge feature 920 of the needle cover 908. In particular, the deformable element 916 is in a flexed or stressed state and abuts an outward facing surface of the ledge feature 920. A part of the deformable element 916 therefore protrudes through the slot 922 and beyond an external circumference of the needle cover 908. A recess may be provided in the body of the medicament delivery device 900 to allow space for the free end of the deformable element 916 in the first configuration. The body may also be shaped so as to have a larger diameter at this point.

The deformable element 916 is placed into the flexed first configuration during manufacture of the medicament delivery device 900 and remains in this state until the device is activated.

Although one deformable element 916 is shown in FIG. 9A, the carrier 914 may comprise two or more deformable elements 916. For example, two deformable elements 916 may be disposed opposite each other on the carrier 914 and may engage with corresponding ledge features 920 in the needle cover 908.

FIG. 9B shows the device 900 with the deformable element 916 in a second configuration. During activation of the device 900, a distal force is applied via the body while the needle cover 908 is placed against the user's skin, causing the needle cover 908 to move proximally into the device 900.

The needle cover 908 thus enters a position between the initial position and the activated position. During this initial movement, the deformable element 916 moves distally over the ledge feature 920. Due to the shaped portion at the free end of the flexible arm, the deformable element 916 may be further flexed radially outwards during this initial movement. Once the needle cover 908 reaches an intermediate position, the free end of the deformable element 916 clears the ledge feature 920 and drops through the slot 920, disengaging the carrier 914 from the needle cover 908. In this manner, movement of the needle cover 908 from the initial position to an intermediate position causes the deformable element 916 to be deformed from the first configuration to the second configuration.

The deformable element 916 is in a relaxed state in the second configuration. The deformable element 916 may be referred to as a permanently deformable element or irreversibly deformable element, since in some examples after the element is deformed, the deformation cannot be reversed. In this embodiment, the deformable element 916 cannot be flexed so as to engage with the ledge feature 920. The deformable element 916 remains in this second configuration for the remainder of the activation movement and throughout device removal. In this example, no part of the deformable element 916 is in contact with the needle cover 908 and thus the deformable element 916 does not exert any normal or friction force on the needle cover 908 in this position. The activation force on the needle cover 908 required after the intermediate position is reached is therefore reduced compared to prior art devices.

The deformable element 916 may produce a sound when it deforms from the first configuration to the second configuration, for example a snapping sound. This may be used to provide feedback to a user or to a sensor within the device 900 or attached to the device 900. The snap sound may be produced by the free end of the deformable element 916 striking another component of the device 900 as it deforms.

Alternatively, or in addition, the deformable element 916 may be configured to produce a vibration when deforming from the first configuration to the second configuration. Again, this may be used to provide feedback to a user or to a sensor within the device 900 or attached to the device 900. The vibration may be produced by the free end of the deformable element 916 striking another component of the device 900 as it deforms.

After the medicament has been delivered, during removal of the device 900, the movement of the needle cover 908 is reversed, but the deformable element 916 remains in its second configuration.

Figure 10:
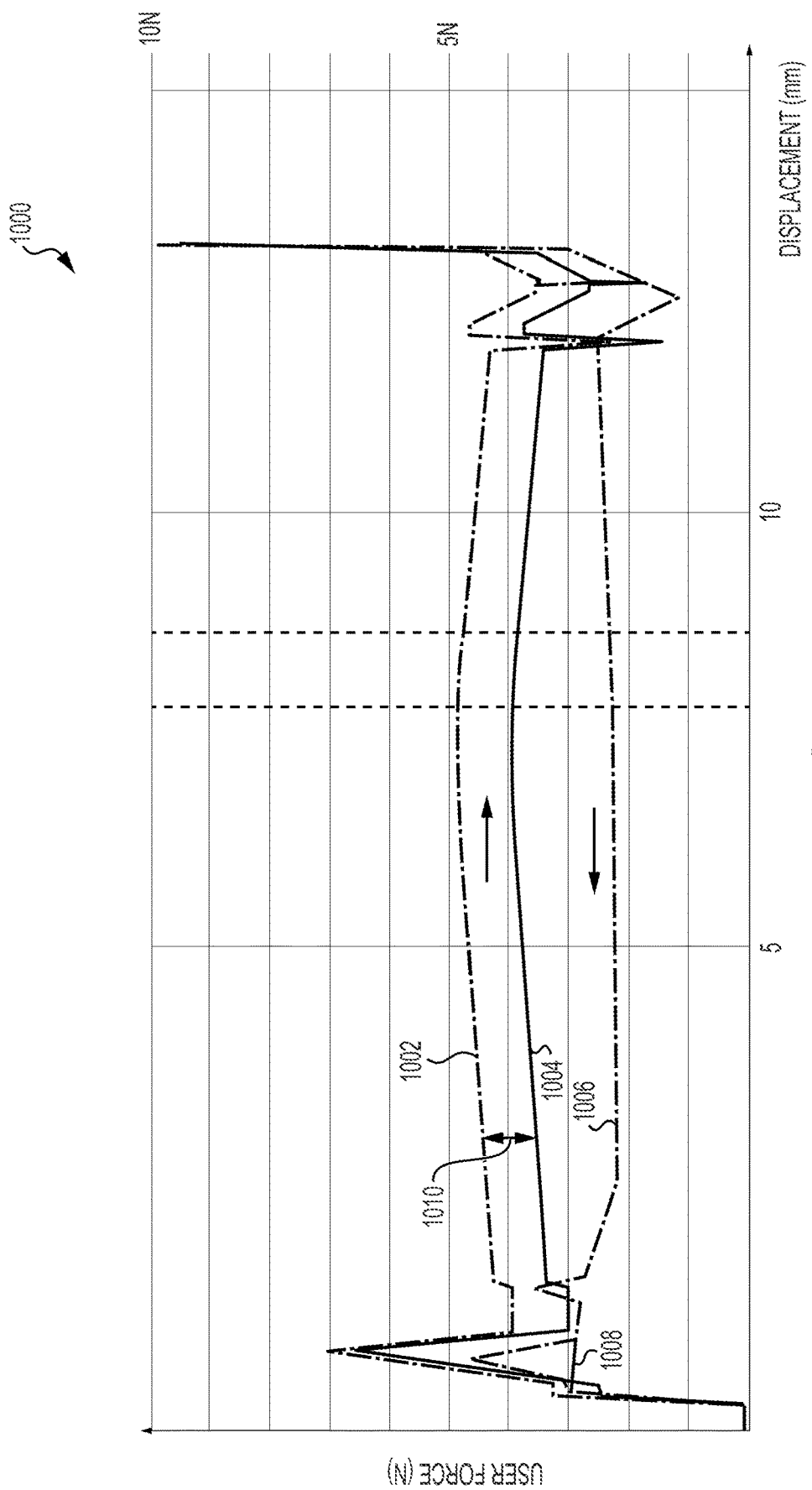
FIG. 10 is a force profile graph illustrating the force profile of a first device and the medicament delivery devices according to the first to fourth embodiments.

Referring to FIG. 10, a force profile graph 1000 is shown illustrating the force profile of a first device 110 and a second device 500, 700, 800, 900. The horizontal axis is the displacement of the needle cover is millimeters (mm) and the vertical axis is the user applied force in Newtons (N).

The first trace 1002 shows the force profile of the activation force of the first device 110 when the user is pushing the device 110 onto their body. The second trace 1004 shows the force profile of the activation force of the medicament delivery device 500, 700, 800, 900, when the user is pushing the device onto their body. The third trace 1006 shows the force profile of the device 110 when the user is removing the device 110 from their body. The fourth trace 1008 shows the force profile of the medicament delivery device 500, 700, 800, 900, when the user is removing the device from their body.

First arrow 712 indicates the difference in activation force between the device 110 and the medicament delivery device 500 during initial movement of the needle cover away from the pre-use position. The lower activation force (of approx. 0.5 N) is achieved by using a spring of lower force to bias the needle cover. The force of the spring is chosen to overcome the frictional forces on the needle cover and cause it to return to the pre-use position when it is removed from the body. As the friction forces in the medicament delivery device 500 as reduced due to the presence of the second slots 602 and relaxed position of the resilient member 516 in the intermediate and activated positions, a weaker spring can be used.

Arrow 1010 indicates the difference in activation force between the device 110 and the medicament delivery device 500, 700, 800, 900 during movement between the intermediate position (occurring at approximately the end of the initial force spike) and the activated position (maximum displacement of the needle cover). The difference is approximately 1 N. As previously mentioned, a spring is used to bias the needle cover in a distal direction relative to the carrier. The force of this spring is chosen to overcome the frictional forces on the needle cover and cause it to return to the pre-use position when it is removed from the body. As the friction forces in the medicament delivery device are reduced due to the use of the deformable element, a weaker spring can be used. This may account for approximately half of the overall reduction in activation force required. The other half of the reduction is accounted for by the lack of friction forces between the carrier and the needle cover after the deformable element has transitioned to the second configuration.

The removal force profile of the medicament delivery device differs from that of the other device at the end of the removal movement, where the resilient member(s) 304 of the carrier 300 re-engage the slots 400 and cause a force spike. This force spike is eliminated in the devices 500, 700, 800, 900 described above because the deformable element remains in the second configuration after the intermediate position during activation.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (SIRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N—(N-lithocholyl-gamma-glutamyl)-des (B30) human insulin; B29-N-(ω-carboxyheptadecanoyl)-des (B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 March-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport 28yndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen.

The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the devices and methods disclosed herein include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1: 2014€. As described in ISO 11608-1: 2014 (E), needle-based injection systems may be broadly distinguished into multi-dose container systems and single-dose (with partial or full evacuation) container systems. The container may be a replaceable container or an integrated non-replaceable container.

As further described in ISO 11608-1: 2014 (E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1: 2014 (E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1: 2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

The invention claimed is:

1. A medicament delivery device comprising:
a body;
a needle for injecting a medicament, the needle disposed at a distal end of the medicament delivery device;
a needle cover axially movable relative to the body between an extended position, in which a distal end of the needle cover is distal to a distal end of the needle, and a retracted position for dispensing the medicament from the medicament delivery device, wherein when the needle cover is in the retracted position the distal end of the needle is distal to the distal end of the needle cover; and
a carrier configured to support a syringe, wherein the carrier is disposed within the needle cover and comprises a deformable element, the deformable element being configured to change from a first configuration in which the deformable element is engaged with the needle cover to a second configuration in which the deformable element is not engaged with the needle cover,
wherein the deformable element is configured
to have a convex shape which protrudes from the carrier towards the needle cover when the deformable element is in the first configuration; and
to have a concave shape which curves away from the needle cover when the deformable element is in the second configuration,
wherein the carrier includes a recess configured to receive at least a part of the deformable element when the deformable element is the concave shape.

2. The medicament delivery device of claim 1, wherein the deformable element is in the first configuration when the needle cover is in the extended position, and the deformable element is in the second configuration when the needle cover is in an intermediate position between the extended position and the retracted position.

3. The medicament delivery device of claim 2, wherein the medicament delivery device is configured such that movement of the needle cover from the extended position to the intermediate position causes the deformable element to be deformed from the first configuration to the second configuration.

4. The medicament delivery device of claim 1, wherein the needle cover comprises a cooperating element, and the deformable element is configured to (i) engage with the cooperating element when the deformable element is in the first configuration and to (ii) be disengaged from the cooperating element when the deformable element is in the second configuration.

5. The medicament delivery device of claim 4, wherein the cooperating element comprises an aperture, a recess, a ridge, or a frictional surface.

6. The medicament delivery device of claim 4, wherein the cooperating element comprises a slot, and the deformable element is configured to abut an edge of the slot when the deformable element is in the first configuration.

7. The medicament delivery device of claim 6, wherein the medicament delivery device is configured such that movement of the needle cover proximally from the extended position causes the deformable element to disengage from the slot.

8. The medicament delivery device of claim 1, wherein the deformable element is configured to produce a sound when changing from the first configuration to the second configuration.

9. The medicament delivery device of claim 1, wherein the deformable element is configured to produce a vibration when changing from the first configuration to the second configuration.

10. The medicament delivery device of claim 1, wherein the deformable element is configured to be deformed from a first shape of the first configuration to a second shape of the second configuration.

11. The medicament delivery device of claim 1, wherein the deformable element is in a stressed state when the deformable element is in the second configuration.

12. The medicament delivery device of claim 1, wherein the deformable element is in a stressed state when the deformable element is in the first configuration.

13. The medicament delivery device of claim 1, wherein there is a zero normal force between the deformable element and the needle cover when the deformable element is in the second configuration.

14. The medicament delivery device of claim 1, further comprising a spring configured to exert a force which biases the needle cover axially towards the distal end of the medicament delivery device.

15. The medicament delivery device of claim 1, further comprising the syringe containing the medicament.

16. A medicament delivery device comprising:
a body;
a needle for injecting a medicament, the needle disposed at a distal end of the medicament delivery device;
a needle cover axially movable relative to the body between an extended position, in which a distal end of the needle cover is distal to a distal end of the needle, and a retracted position for dispensing the medicament from the medicament delivery device, wherein when the needle cover is in the retracted position the distal end of the needle is distal to the distal end of the needle cover; and
a carrier configured to support a syringe, wherein the carrier is disposed within the needle cover and comprises two or more deformable elements, the two or more deformable elements being configured to change from a first configuration in which each deformable element of the two or more deformable elements is engaged with the needle cover to a second configuration in which each deformable element of the two or more deformable elements is not engaged with the needle cover,
wherein each deformable element of the two or more deformable elements is configured
to have a convex shape which protrudes from the carrier towards the needle cover when each deformable element of the two or more deformable elements is in the first configuration; and
to have a concave shape which curves away from the needle cover when each deformable element of the two or more deformable elements is in the second configuration,
wherein the carrier includes a recess configured to receive at least a part of each deformable element of the two or more deformable elements when each deformable element of the two or more deformable elements is the concave shape.

17. The medicament delivery device of claim 16, wherein the needle cover comprises two or more cooperating elements, and each deformable element of the two or more deformable elements is configured to engage with a respective cooperating element of the two or more cooperating elements when each deformable element of the two or more deformable elements is in the first configuration and to be disengaged from the respective cooperating element when each deformable element of the two or more deformable elements is in the second configuration.

18. A medicament delivery device comprising:
a body;
a needle for injecting a medicament, the needle disposed at a distal end of the medicament delivery device;
a needle cover configured to be moved in a proximal direction into the body of the medicament delivery device to expose a distal end of the needle from a distal end of the needle cover; and
a syringe carrier disposed within the needle cover and comprising a deformable element,
wherein the deformable element is configured such that
prior to a movement of the needle cover relative to the body of the medicament delivery device, the deformable element has a first configuration in which the deformable element is engaged with the needle cover;
during an initial portion of the movement of the needle cover relative to the body, the deformable element is forced to deform into a second configuration by the movement of the needle cover such that the deformable element is not engaged with the needle cover; and
for a remainder of the movement of the needle cover relative to the body, the deformable element remains in the second configuration,
wherein the deformable element is configured
to have a convex shape which protrudes from the syringe carrier towards the needle cover when the deformable element is in the first configuration; and
to have a concave shape which curves away from the needle cover when the deformable element is in the second configuration,
wherein the syringe carrier includes a recess configured to receive at least a part of the deformable element when the deformable element is the concave shape.

19. The medicament delivery device of claim 18, wherein the deformable element is configured to permanently deform into the second configuration.

20. The medicament delivery device of claim 18, wherein the deformable element is configured to be deformed from a first shape of the first configuration to a second shape of the second configuration.

21. The medicament delivery device of claim 18, wherein the deformable element is in a stressed state when the deformable element is in the first configuration.

\* \* \* \* \*